(12) United States Patent
Baker, Jr. et al.

(10) Patent No.: US 8,509,869 B2
(45) Date of Patent: Aug. 13, 2013

(54) METHOD AND APPARATUS FOR DETECTING AND ANALYZING VARIATIONS IN A PHYSIOLOGIC PARAMETER

(75) Inventors: Clark R. Baker, Jr., Newman, CA (US); Paul D. Mannheimer, Danville, CA (US)

(73) Assignee: Covidien LP, Mansfield, MA (US)

( * ) Notice: Subject to any disclaimer, the term of this patent is extended or adjusted under 35 U.S.C. 154(b) by 1112 days.

(21) Appl. No.: 12/467,003

(22) Filed: May 15, 2009

(65) Prior Publication Data
US 2010/0292548 A1 Nov. 18, 2010

(51) Int. Cl.
*A61B 5/00* (2006.01)

(52) U.S. Cl.
USPC ........................................................ 600/323

(58) Field of Classification Search
USPC ............. 128/204.23, 204.18, 204.26, 205.24; 600/309, 310, 323, 338, 328, 330, 300, 301; 604/66; 709/201
See application file for complete search history.

(56) References Cited

U.S. PATENT DOCUMENTS

| | | |
|---|---|---|
| 3,638,640 A | 2/1972 | Shaw |
| 3,721,813 A | 3/1973 | Condon et al. |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,685,464 A | 8/1987 | Goldberger et al. |
| 4,694,833 A | 9/1987 | Hamaguri |
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,796,636 A | 1/1989 | Branstetter et al. |
| 4,800,495 A | 1/1989 | Smith |

(Continued)

FOREIGN PATENT DOCUMENTS

| | | |
|---|---|---|
| DE | 3405444 | 8/1985 |
| DE | 69123448 | 5/1997 |

(Continued)

OTHER PUBLICATIONS

U.S. Appl. No. 12/165,230, filed Jun. 30, 2008, Baker, Jr.

(Continued)

*Primary Examiner* — Brian Szmal (57) ABSTRACT

The present disclosure is generally directed to identifying and/or analyzing high resolution variations in a measured physiologic parameter, such as blood oxygen saturation ($SpO_2$) measured using pulse oximetry. Present embodiments may include a system including a sensor comprising an emitter capable of emitting light at different wavelengths into a tissue bed, and a detector capable of detecting the light from the emitter after dispersion and/or reflection by the tissue bed. Further, the system may include a pulse oximeter capable of receiving signals from the sensor that are indicative of characteristics of the light detected by the detector, and utilizing the signals to estimate blood oxygen saturation values over time at a high resolution to facilitate detection of variations in the blood oxygen saturation values that are smaller in magnitude than an accuracy, display precision, and/or calibration of the blood oxygen saturation values.

17 Claims, 5 Drawing Sheets

(56) References Cited

U.S. PATENT DOCUMENTS

| | | |
|---|---|---|
| 4,800,885 A | 1/1989 | Johnson |
| 4,802,486 A | 2/1989 | Goodman et al. |
| 4,805,623 A | 2/1989 | Jobsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hausman et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,936,679 A | 6/1990 | Mersch |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,972,331 A | 11/1990 | Chance |
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,035,243 A | 7/1991 | Muz |
| 5,040,039 A | 8/1991 | Hattori et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,084,327 A | 1/1992 | Stengel |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H1039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| 5,119,815 A | 6/1992 | Chance |
| 5,122,974 A | 6/1992 | Chance |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,167,230 A | 12/1992 | Chance |
| 5,170,786 A | 12/1992 | Thomas et al. |
| 5,188,108 A | 2/1993 | Secker |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp |
| 5,216,598 A | 6/1993 | Branstetter et al. |
| 5,217,012 A | 6/1993 | Young et al. |
| 5,217,013 A | 6/1993 | Lewis et al. |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Friedman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,273,036 A | 12/1993 | Kronberg et al. |
| 5,275,159 A | 1/1994 | Griebel |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Friedman et al. |
| 5,311,865 A | 5/1994 | Mayeux |
| 5,313,940 A | 5/1994 | Fuse et al. |
| 5,323,776 A | 6/1994 | Blakeley et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |
| 5,349,519 A | 9/1994 | Kaestle |
| 5,349,952 A | 9/1994 | McCarthy et al. |
| 5,349,953 A | 9/1994 | McCarthy et al. |
| 5,351,685 A | 10/1994 | Potratz |
| 5,353,799 A | 10/1994 | Chance |
| 5,355,880 A | 10/1994 | Thomas et al. |
| 5,355,882 A | 10/1994 | Ukawa et al. |
| 5,361,758 A | 11/1994 | Hall et al. |
| 5,365,066 A | 11/1994 | Krueger, Jr. et al. |
| 5,368,025 A | 11/1994 | Young et al. |
| 5,368,026 A | 11/1994 | Swedlow et al. |
| 5,368,224 A | 11/1994 | Richardson et al. |
| 5,372,136 A | 12/1994 | Steuer et al. |
| 5,377,675 A | 1/1995 | Ruskewicz et al. |
| 5,385,143 A | 1/1995 | Aoyagi |
| 5,387,122 A | 2/1995 | Goldberger et al. |
| 5,390,670 A | 2/1995 | Centa et al. |
| 5,392,777 A | 2/1995 | Swedlow et al. |
| 5,398,680 A | 3/1995 | Polson et al. |
| 5,402,777 A | 4/1995 | Warring et al. |
| 5,411,023 A | 5/1995 | Morris, Sr. et al. |
| 5,411,024 A | 5/1995 | Thomas et al. |
| 5,413,099 A | 5/1995 | Schmidt et al. |
| 5,413,100 A | 5/1995 | Barthelemy et al. |

| | | |
|---|---|---|
| 5,413,101 A | 5/1995 | Sugiura |
| 5,413,102 A | 5/1995 | Schmidt et al. |
| 5,417,207 A | 5/1995 | Young et al. |
| 5,421,329 A | 6/1995 | Casciani et al. |
| 5,425,360 A | 6/1995 | Nelson |
| 5,425,362 A | 6/1995 | Siker et al. |
| 5,427,093 A | 6/1995 | Ogawa et al. |
| 5,429,128 A | 7/1995 | Cadell et al. |
| 5,429,129 A | 7/1995 | Lovejoy et al. |
| 5,431,159 A | 7/1995 | Baker et al. |
| 5,431,170 A | 7/1995 | Mathews |
| 5,437,275 A | 8/1995 | Amundsen et al. |
| 5,438,986 A | 8/1995 | Disch et al. |
| 5,448,991 A | 9/1995 | Polson et al. |
| 5,452,717 A | 9/1995 | Branigan et al. |
| 5,465,714 A | 11/1995 | Scheuing |
| 5,469,845 A | 11/1995 | DeLonzor et al. |
| RE35,122 E | 12/1995 | Corenman et al. |
| 5,474,065 A | 12/1995 | Meathrel et al. |
| 5,482,034 A | 1/1996 | Lewis et al. |
| 5,482,036 A | 1/1996 | Diab et al. |
| 5,483,646 A | 1/1996 | Uchikoga |
| 5,485,847 A | 1/1996 | Baker, Jr. |
| 5,490,505 A | 2/1996 | Diab et al. |
| 5,490,523 A | 2/1996 | Isaacson et al. |
| 5,491,299 A | 2/1996 | Naylor et al. |
| 5,494,032 A | 2/1996 | Robinson et al. |
| 5,497,771 A | 3/1996 | Rosenheimer |
| 5,499,627 A | 3/1996 | Steuer et al. |
| 5,503,148 A | 4/1996 | Pologe et al. |
| 5,505,199 A | 4/1996 | Kim |
| 5,507,286 A | 4/1996 | Solenberger |
| 5,511,546 A | 4/1996 | Hon |
| 5,517,988 A | 5/1996 | Gerhard |
| 5,520,177 A | 5/1996 | Ogawa et al. |
| 5,521,851 A | 5/1996 | Wei et al. |
| 5,522,388 A | 6/1996 | Ishikawa et al. |
| 5,524,617 A | 6/1996 | Mannheimer |
| 5,529,064 A | 6/1996 | Rall et al. |
| 5,533,507 A | 7/1996 | Potratz et al. |
| 5,551,423 A | 9/1996 | Sugiura |
| 5,551,424 A | 9/1996 | Morrison et al. |
| 5,553,614 A | 9/1996 | Chance |
| 5,553,615 A | 9/1996 | Carim et al. |
| 5,555,882 A | 9/1996 | Richardson et al. |
| 5,558,096 A | 9/1996 | Palatnik |
| 5,560,355 A | 10/1996 | Merchant et al. |
| 5,564,417 A | 10/1996 | Chance |
| 5,575,284 A | 11/1996 | Athan et al. |
| 5,575,285 A | 11/1996 | Takanashi et al. |
| 5,577,500 A | 11/1996 | Potratz |
| 5,582,169 A | 12/1996 | Oda et al. |
| 5,584,296 A | 12/1996 | Cui et al. |
| 5,588,425 A | 12/1996 | Sackner et al. |
| 5,588,427 A | 12/1996 | Tien |
| 5,590,652 A | 1/1997 | Inai |
| 5,595,176 A | 1/1997 | Yamaura |
| 5,596,986 A | 1/1997 | Goldfarb |
| 5,611,337 A | 3/1997 | Bukta |
| 5,617,852 A | 4/1997 | MacGregor |
| 5,619,992 A | 4/1997 | Guthrie et al. |
| 5,626,140 A | 5/1997 | Feldman et al. |
| 5,630,413 A | 5/1997 | Thomas et al. |
| 5,632,272 A | 5/1997 | Diab et al. |
| 5,632,273 A | 5/1997 | Suzuki |
| 5,634,459 A | 6/1997 | Gardosi |
| 5,638,593 A | 6/1997 | Gerhardt et al. |
| 5,638,818 A | 6/1997 | Diab et al. |
| 5,645,059 A | 7/1997 | Fein et al. |
| 5,645,060 A | 7/1997 | Yorkey et al. |
| 5,645,440 A | 7/1997 | Tobler et al. |
| 5,660,567 A | 8/1997 | Nierlich et al. |
| 5,662,105 A | 9/1997 | Tien |
| 5,662,106 A | 9/1997 | Swedlow et al. |
| 5,666,952 A | 9/1997 | Fuse et al. |
| 5,671,529 A | 9/1997 | Nelson |
| 5,673,692 A | 10/1997 | Schulze et al. |
| 5,673,693 A | 10/1997 | Solenberger |
| 5,676,139 A | 10/1997 | Goldberger et al. |
| 5,676,141 A | 10/1997 | Hollub |
| 5,678,544 A | 10/1997 | DeLonzor et al. |
| 5,680,857 A | 10/1997 | Pelikan et al. |
| 5,685,299 A | 11/1997 | Diab et al. |
| 5,685,301 A | 11/1997 | Klomhaus |
| 5,687,719 A | 11/1997 | Sato et al. |
| 5,687,722 A | 11/1997 | Tien et al. |
| 5,692,503 A | 12/1997 | Kuenstner |
| 5,692,505 A | 12/1997 | Fouts |
| 5,709,205 A | 1/1998 | Bukta |
| 5,713,355 A | 2/1998 | Richardson et al. |
| 5,724,967 A | 3/1998 | Venkatachalam |
| 5,727,547 A | 3/1998 | Levinson et al. |
| 5,730,124 A | 3/1998 | Yamauchi |
| 5,731,582 A | 3/1998 | West |
| 393,830 | 4/1998 | Tobler et al. |
| 5,743,260 A | 4/1998 | Chung et al. |
| 5,743,263 A | 4/1998 | Baker, Jr. |
| 5,746,206 A | 5/1998 | Mannheimer |
| 5,746,697 A | 5/1998 | Swedlow et al. |
| 5,752,914 A | 5/1998 | DeLonzor et al. |
| 5,755,226 A | 5/1998 | Carim et al. |
| 5,758,644 A | 6/1998 | Diab et al. |
| 5,760,910 A | 6/1998 | Lepper, Jr. et al. |
| 5,766,125 A | 6/1998 | Aoyagi et al. |
| 5,766,127 A | 6/1998 | Pologe et al. |
| 5,769,785 A | 6/1998 | Diab et al. |
| 5,772,587 A | 6/1998 | Gratton et al. |
| 5,774,213 A | 6/1998 | Trebino et al. |
| 5,776,058 A | 7/1998 | Levinson et al. |
| 5,776,059 A | 7/1998 | Kaestle |
| 5,779,630 A | 7/1998 | Fein et al. |
| 5,779,631 A | 7/1998 | Chance |
| 5,782,237 A | 7/1998 | Casciani et al. |
| 5,782,756 A | 7/1998 | Mannheimer |
| 5,782,757 A | 7/1998 | Diab et al. |
| 5,782,758 A | 7/1998 | Ausec et al. |
| 5,786,592 A | 7/1998 | Hök |
| 5,790,729 A | 8/1998 | Pologe et al. |
| 5,792,052 A | 8/1998 | Isaacson et al. |
| 5,795,292 A | 8/1998 | Lewis et al. |
| 5,797,841 A | 8/1998 | DeLonzor et al. |
| 5,800,348 A | 9/1998 | Kaestle |
| 5,800,349 A | 9/1998 | Isaacson et al. |
| 5,803,910 A | 9/1998 | Potratz |
| 5,807,246 A | 9/1998 | Sakaguchi et al. |
| 5,807,247 A | 9/1998 | Merchant et al. |
| 5,807,248 A | 9/1998 | Mills |
| 5,810,723 A | 9/1998 | Aldrich |
| 5,810,724 A | 9/1998 | Gronvall |
| 5,813,980 A | 9/1998 | Levinson et al. |
| 5,817,008 A | 10/1998 | Rafert et al. |
| 5,817,009 A | 10/1998 | Rosenheimer et al. |
| 5,817,010 A | 10/1998 | Hibl |
| 5,818,985 A | 10/1998 | Merchant et al. |
| 5,820,550 A | 10/1998 | Polson et al. |
| 5,823,950 A | 10/1998 | Diab et al. |
| 5,823,952 A | 10/1998 | Levinson et al. |
| 5,827,182 A | 10/1998 | Raley et al. |
| 5,830,135 A | 11/1998 | Bosque et al. |
| 5,830,136 A | 11/1998 | DeLonzor et al. |
| 5,830,137 A | 11/1998 | Scharf |
| 5,830,139 A | 11/1998 | Abreu |
| 5,831,598 A | 11/1998 | Kauffert et al. |
| 5,839,439 A | 11/1998 | Nierlich et al. |
| RE36,000 E | 12/1998 | Swedlow et al. |
| 5,842,979 A | 12/1998 | Jarman et al. |
| 5,842,981 A | 12/1998 | Larsen et al. |
| 5,842,982 A | 12/1998 | Mannheimer |
| 5,846,190 A | 12/1998 | Woehrle |
| 5,851,178 A | 12/1998 | Aronow |
| 5,851,179 A | 12/1998 | Ritson et al. |
| 5,853,364 A | 12/1998 | Baker, Jr. et al. |
| 5,860,919 A | 1/1999 | Kiani-Azarbayjany et al. |
| 5,865,736 A | 2/1999 | Baker, Jr. et al. |
| 5,871,442 A | 2/1999 | Madarasz et al. |
| 5,873,821 A | 2/1999 | Chance et al. |
| 5,879,294 A | 3/1999 | Anderson et al. |
| 5,885,213 A | 3/1999 | Richardson et al. |

| Patent | Date | Inventor |
|---|---|---|
| 5,890,929 A | 4/1999 | Mills et al. |
| 5,891,021 A | 4/1999 | Dillon et al. |
| 5,891,022 A | 4/1999 | Pologe |
| 5,891,024 A | 4/1999 | Jarman et al. |
| 5,891,025 A | 4/1999 | Buschmann et al. |
| 5,891,026 A | 4/1999 | Wang et al. |
| 5,902,235 A | 5/1999 | Lewis et al. |
| 5,910,108 A | 6/1999 | Solenberger |
| 5,911,690 A | 6/1999 | Rall |
| 5,912,656 A | 6/1999 | Tham et al. |
| 5,913,819 A | 6/1999 | Taylor et al. |
| 5,916,154 A | 6/1999 | Hobbs et al. |
| 5,916,155 A | 6/1999 | Levinson et al. |
| 5,919,133 A | 7/1999 | Taylor et al. |
| 5,919,134 A | 7/1999 | Diab |
| 5,920,263 A | 7/1999 | Huttenhoff et al. |
| 5,921,921 A | 7/1999 | Potratz et al. |
| 5,922,607 A | 7/1999 | Bernreuter |
| 5,924,979 A | 7/1999 | Swedlow et al. |
| 5,924,980 A | 7/1999 | Coetzee |
| 5,924,982 A | 7/1999 | Chin |
| 5,924,985 A | 7/1999 | Jones |
| 5,934,277 A | 8/1999 | Mortz |
| 5,934,925 A | 8/1999 | Tobler et al. |
| 5,940,182 A | 8/1999 | Lepper, Jr. et al. |
| 5,954,644 A | 9/1999 | Dettling et al. |
| 5,960,610 A | 10/1999 | Levinson et al. |
| 5,961,450 A | 10/1999 | Merchant et al. |
| 5,961,452 A | 10/1999 | Chung et al. |
| 5,964,701 A | 10/1999 | Asada et al. |
| 5,971,930 A | 10/1999 | Elghazzawi |
| 5,978,691 A | 11/1999 | Mills |
| 5,978,693 A | 11/1999 | Hamilton et al. |
| 5,983,122 A | 11/1999 | Jarman et al. |
| 5,987,343 A | 11/1999 | Kinast |
| 5,991,648 A | 11/1999 | Levin |
| 5,995,855 A | 11/1999 | Kiani et al. |
| 5,995,856 A | 11/1999 | Mannheimer et al. |
| 5,995,858 A | 11/1999 | Kinast |
| 5,995,859 A | 11/1999 | Takahashi |
| 5,997,343 A | 12/1999 | Mills et al. |
| 5,999,834 A | 12/1999 | Wang et al. |
| 6,002,952 A | 12/1999 | Diab et al. |
| 6,005,658 A | 12/1999 | Kaluza et al. |
| 6,006,120 A | 12/1999 | Levin |
| 6,011,985 A | 1/2000 | Athan et al. |
| 6,011,986 A | 1/2000 | Diab et al. |
| 6,014,576 A | 1/2000 | Raley et al. |
| 6,018,673 A | 1/2000 | Chin et al. |
| 6,018,674 A | 1/2000 | Aronow |
| 6,022,321 A | 2/2000 | Amano et al. |
| 6,023,541 A | 2/2000 | Merchant et al. |
| 6,026,312 A | 2/2000 | Shemwell et al. |
| 6,026,314 A | 2/2000 | Amerov et al. |
| 6,031,603 A | 2/2000 | Fine et al. |
| 6,035,223 A | 3/2000 | Baker, Jr. |
| 6,036,642 A | 3/2000 | Diab et al. |
| 6,041,247 A | 3/2000 | Weckstrom et al. |
| 6,044,283 A | 3/2000 | Fein et al. |
| 6,047,201 A | 4/2000 | Jackson, III |
| 6,061,584 A | 5/2000 | Lovejoy et al. |
| 6,064,898 A | 5/2000 | Aldrich |
| 6,064,899 A | 5/2000 | Fein et al. |
| 6,067,462 A | 5/2000 | Diab et al. |
| 6,073,038 A | 6/2000 | Wang et al. |
| 6,078,833 A | 6/2000 | Hueber |
| 6,081,735 A | 6/2000 | Diab et al. |
| 6,081,742 A | 6/2000 | Amano et al. |
| 6,083,157 A | 7/2000 | Noller |
| 6,083,172 A | 7/2000 | Baker, Jr. et al. |
| 6,088,607 A | 7/2000 | Diab et al. |
| 6,094,592 A | 7/2000 | Yorkey et al. |
| 6,095,974 A | 8/2000 | Shemwell et al. |
| 6,104,938 A | 8/2000 | Huiku et al. |
| 6,112,107 A | 8/2000 | Hannula |
| 6,113,541 A | 9/2000 | Dias et al. |
| 6,115,621 A | 9/2000 | Chin |
| 6,120,460 A | 9/2000 | Abreu |
| 6,122,535 A | 9/2000 | Kaestle et al. |
| 6,133,994 A | 10/2000 | Mathews et al. |
| 6,134,460 A | 10/2000 | Chance |
| 6,135,952 A | 10/2000 | Coetzee |
| 6,144,444 A | 11/2000 | Haworth et al. |
| 6,144,867 A | 11/2000 | Walker et al. |
| 6,144,868 A | 11/2000 | Parker |
| 6,149,481 A | 11/2000 | Wang et al. |
| 6,150,951 A | 11/2000 | Olejniczak |
| 6,151,107 A | 11/2000 | Schöllermann et al. |
| 6,151,516 A | 11/2000 | Kiani-Azarbayjany et al. |
| 6,151,518 A | 11/2000 | Hayashi |
| 6,152,754 A | 11/2000 | Gerhardt et al. |
| 6,154,667 A | 11/2000 | Miura et al. |
| 6,157,850 A | 12/2000 | Diab et al. |
| 6,163,715 A | 12/2000 | Larsen et al. |
| 6,165,005 A | 12/2000 | Mills et al. |
| 6,173,196 B1 | 1/2001 | Delonzor et al. |
| 6,178,343 B1 | 1/2001 | Bindszus et al. |
| 6,181,958 B1 | 1/2001 | Steuer et al. |
| 6,181,959 B1 | 1/2001 | Schöllermann et al. |
| 6,184,521 B1 | 2/2001 | Coffin, IV et al. |
| 6,188,470 B1 | 2/2001 | Grace |
| 6,192,260 B1 | 2/2001 | Chance |
| 6,195,575 B1 | 2/2001 | Levinson |
| 6,198,951 B1 | 3/2001 | Kosuda et al. |
| 6,206,830 B1 | 3/2001 | Diab et al. |
| 6,213,952 B1 | 4/2001 | Finarov et al. |
| 6,217,523 B1 | 4/2001 | Amano et al. |
| 6,222,189 B1 | 4/2001 | Misner et al. |
| 6,226,539 B1 | 5/2001 | Potratz |
| 6,226,540 B1 | 5/2001 | Bernreuter et al. |
| 6,229,856 B1 | 5/2001 | Diab et al. |
| 6,230,035 B1 | 5/2001 | Aoyagi et al. |
| 6,233,470 B1 | 5/2001 | Tsuchiya |
| 6,236,871 B1 | 5/2001 | Tsuchiya |
| 6,236,872 B1 | 5/2001 | Diab et al. |
| 6,240,305 B1 | 5/2001 | Tsuchiya |
| 6,253,097 B1 | 6/2001 | Aronow et al. |
| 6,253,098 B1 | 6/2001 | Walker et al. |
| 6,256,523 B1 | 7/2001 | Diab et al. |
| 6,256,524 B1 | 7/2001 | Walker et al. |
| 6,261,236 B1 | 7/2001 | Grimblatov |
| 6,263,221 B1 | 7/2001 | Chance et al. |
| 6,263,222 B1 | 7/2001 | Diab et al. |
| 6,263,223 B1 | 7/2001 | Shepherd et al. |
| 6,266,546 B1 | 7/2001 | Steuer et al. |
| 6,266,547 B1 | 7/2001 | Walker et al. |
| 6,272,363 B1 | 8/2001 | Casciani et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,894 B1 | 9/2001 | Oppelt et al. |
| 6,285,895 B1 | 9/2001 | Ristolainen et al. |
| 6,285,896 B1 | 9/2001 | Tobler et al. |
| 6,298,252 B1 | 10/2001 | Kovach et al. |
| 6,308,089 B1 | 10/2001 | Von der Ruhr et al. |
| 6,312,393 B1 | 11/2001 | Abreu |
| 6,321,100 B1 | 11/2001 | Parker |
| 6,330,468 B1 | 12/2001 | Scharf |
| 6,334,065 B1 | 12/2001 | Al-Ali et al. |
| 6,339,715 B1 | 1/2002 | Bahr et al. |
| 6,343,223 B1 | 1/2002 | Chin et al. |
| 6,343,224 B1 | 1/2002 | Parker |
| 6,349,228 B1 | 2/2002 | Kiani et al. |
| 6,351,658 B1 | 2/2002 | Middleman et al. |
| 6,353,750 B1 | 3/2002 | Kimura et al. |
| 6,356,774 B1 | 3/2002 | Bernstein et al. |
| 6,360,113 B1 | 3/2002 | Dettling |
| 6,360,114 B1 | 3/2002 | Diab et al. |
| 6,361,501 B1 | 3/2002 | Amano et al. |
| 6,363,269 B1 | 3/2002 | Hanna et al. |
| 6,370,408 B1 | 4/2002 | Merchant et al. |
| 6,370,409 B1 | 4/2002 | Chung et al. |
| 6,374,129 B1 | 4/2002 | Chin et al. |
| 6,377,829 B1 | 4/2002 | Al-Ali et al. |
| 6,381,479 B1 | 4/2002 | Norris |
| 6,381,480 B1 | 4/2002 | Stoddart et al. |
| 6,385,471 B1 | 5/2002 | Mortz |
| 6,385,821 B1 | 5/2002 | Modgil et al. |

| | | |
|---|---|---|
| 6,388,240 B2 | 5/2002 | Schulz et al. |
| 6,393,310 B1 | 5/2002 | Kuenstner |
| 6,397,091 B2 | 5/2002 | Diab et al. |
| 6,397,092 B1 | 5/2002 | Norris et al. |
| 6,397,093 B1 | 5/2002 | Aldrich |
| 6,400,971 B1 | 6/2002 | Finarov et al. |
| 6,400,972 B1 | 6/2002 | Fine |
| 6,402,690 B1 | 6/2002 | Rhee et al. |
| 6,408,198 B1 | 6/2002 | Hanna et al. |
| 6,411,832 B1 | 6/2002 | Guthermann |
| 6,411,833 B1 | 6/2002 | Baker, Jr. et al. |
| 6,415,236 B2 | 7/2002 | Kobayashi et al. |
| 6,419,671 B1 | 7/2002 | Lemberg |
| 6,421,549 B1 | 7/2002 | Jacques |
| 6,430,423 B2 | 8/2002 | DeLonzor et al. |
| 6,430,513 B1 | 8/2002 | Wang et al. |
| 6,430,525 B1 | 8/2002 | Weber et al. |
| 6,434,408 B1 | 8/2002 | Heckel |
| 6,438,399 B1 | 8/2002 | Kurth |
| 6,449,501 B1 | 9/2002 | Reuss |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B1 | 10/2002 | Walker et al. |
| 6,480,729 B2 | 11/2002 | Stone |
| 6,490,466 B1 | 12/2002 | Fein et al. |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,546,267 B1 | 4/2003 | Sugiura et al. |
| 6,549,795 B1 | 4/2003 | Chance |
| 6,553,241 B2 | 4/2003 | Mannheimer et al. |
| 6,553,242 B1 | 4/2003 | Sarussi |
| 6,553,243 B2 | 4/2003 | Gurley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,509 B2 | 8/2003 | Schmitt |
| 6,606,510 B2 | 8/2003 | Swedlow et al. |
| 6,606,511 B1 | 8/2003 | Ali et al. |
| 6,606,512 B2 | 8/2003 | Muz et al. |
| 6,615,064 B1 | 9/2003 | Aldrich |
| 6,615,065 B1 | 9/2003 | Barrett et al. |
| 6,618,042 B1 | 9/2003 | Powell |
| 6,618,602 B2 | 9/2003 | Levin et al. |
| 6,622,034 B1 | 9/2003 | Gorski et al. |
| 6,622,095 B2 | 9/2003 | Kobayashi et al. |
| 6,628,975 B1 | 9/2003 | Fein et al. |
| 6,631,281 B1 | 10/2003 | Kästle |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wasserman |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B2 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neill et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,760,610 B2 | 7/2004 | Tschupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |

| Patent | Date | Name |
|---|---|---|
| 6,773,397 B2 | 8/2004 | Kelly |
| 6,778,923 B2 | 8/2004 | Norris et al. |
| 6,780,158 B2 | 8/2004 | Yarita |
| 6,791,689 B1 | 9/2004 | Weckström |
| 6,792,300 B1 | 9/2004 | Diab et al. |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,053 B2 | 2/2005 | Daalmans et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,873,865 B2 | 3/2005 | Steuer et al. |
| 6,879,850 B2 | 4/2005 | Kimball |
| 6,882,874 B2 | 4/2005 | Huiku |
| 6,889,153 B2 | 5/2005 | Dietiker |
| 6,898,451 B2 | 5/2005 | Wuori |
| 6,898,452 B2 | 5/2005 | Al-Ali et al. |
| 6,909,912 B2 | 6/2005 | Melker et al. |
| 6,912,413 B2 | 6/2005 | Rantala et al. |
| 6,916,289 B2 | 7/2005 | Schnall |
| 6,920,345 B2 | 7/2005 | Al-Ali et al. |
| 6,931,268 B1 | 8/2005 | Kiani-Azarbayjany et al. |
| 6,931,269 B2 | 8/2005 | Terry |
| 6,934,570 B2 | 8/2005 | Kiani et al. |
| 6,939,307 B1 | 9/2005 | Dunlop |
| 6,941,162 B2 | 9/2005 | Fudge et al. |
| 6,947,780 B2 | 9/2005 | Scharf |
| 6,947,781 B2 | 9/2005 | Asada et al. |
| 6,950,687 B2 | 9/2005 | Al-Ali |
| 6,961,598 B2 | 11/2005 | Diab |
| 6,963,767 B2 | 11/2005 | Rantala et al. |
| 6,971,580 B2 | 12/2005 | DeLonzor et al. |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Al-Ali |
| 6,992,772 B2 | 1/2006 | Block et al. |
| 6,993,371 B2 | 1/2006 | Kiani et al. |
| 6,993,372 B2 | 1/2006 | Fine et al. |
| 6,996,427 B2 | 2/2006 | Ali et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,010,341 B2 | 3/2006 | Chance |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali et al. |
| 7,027,850 B2 | 4/2006 | Wasserman |
| 7,030,749 B2 | 4/2006 | Al-Ali |
| 7,035,697 B1 | 4/2006 | Brown |
| 7,039,449 B2 | 5/2006 | Al-Ali |
| 7,043,289 B2 | 5/2006 | Fine et al. |
| 7,047,055 B2 | 5/2006 | Boas et al. |
| 7,047,056 B2 | 5/2006 | Hannula et al. |
| 7,060,035 B2 | 6/2006 | Wasserman |
| 7,062,307 B2 | 6/2006 | Norris et al. |
| 7,067,893 B2 | 6/2006 | Mills et al. |
| 7,072,701 B2 | 7/2006 | Chen et al. |
| 7,072,702 B2 | 7/2006 | Edgar, Jr. et al. |
| 7,079,880 B2 | 7/2006 | Stetson |
| 7,085,597 B2 | 8/2006 | Fein et al. |
| 7,096,052 B2 | 8/2006 | Mason et al. |
| 7,096,054 B2 | 8/2006 | Abdul-Hafiz et al. |
| 7,107,088 B2 | 9/2006 | Aceti |
| 7,113,815 B2 | 9/2006 | O'Neil et al. |
| 7,123,950 B2 | 10/2006 | Mannheimer |
| 7,127,278 B2 | 10/2006 | Melker et al. |
| 7,130,671 B2 | 10/2006 | Baker, Jr. et al. |
| 7,132,641 B2 | 11/2006 | Schulz et al. |
| 7,133,711 B2 | 11/2006 | Chernoguz et al. |
| 7,139,599 B2 | 11/2006 | Terry |
| 7,142,142 B2 | 11/2006 | Petersen et al. |
| 7,142,901 B2 | 11/2006 | Kiani et al. |
| 7,162,288 B2 | 1/2007 | Nordstrom |
| 7,162,306 B2 | 1/2007 | Caby et al. |
| 7,184,809 B1 | 2/2007 | Sterling et al. |
| 7,190,987 B2 | 3/2007 | Lindekugel et al. |
| 7,198,778 B2 | 4/2007 | Mannheimer et al. |
| 7,209,775 B2 | 4/2007 | Bae et al. |
| 7,215,984 B2 | 5/2007 | Diab et al. |
| 7,225,006 B2 | 5/2007 | Al-Ali et al. |
| 7,236,811 B2 | 6/2007 | Schmitt |
| 7,239,905 B2 | 7/2007 | Kiani-Azarbayjany et al. |
| 7,248,910 B2 | 7/2007 | Li et al. |
| 7,251,518 B2 | 7/2007 | Herrmann |
| 7,254,433 B2 | 8/2007 | Diab et al. |
| 7,254,434 B2 | 8/2007 | Schulz et al. |
| 7,263,395 B2 | 8/2007 | Chan et al. |
| 7,272,426 B2 | 9/2007 | Schmid |
| 7,280,858 B2 | 10/2007 | Al-Ali et al. |
| 7,295,866 B2 | 11/2007 | Al-Ali et al. |
| 7,302,284 B2 | 11/2007 | Baker, Jr. et al. |
| 7,305,262 B2 | 12/2007 | Brodnick et al. |
| 7,315,753 B2 | 1/2008 | Baker, Jr. et al. |
| 7,336,983 B2 | 2/2008 | Baker, Jr. et al. |
| 7,355,539 B2 | 4/2008 | Petersen et al. |
| 7,373,193 B2 | 5/2008 | Al-Ali et al. |
| 7,477,571 B2 | 1/2009 | Melese et al. |
| 2001/0005773 A1 | 6/2001 | Larsen et al. |
| 2001/0020122 A1 | 9/2001 | Steuer et al. |
| 2001/0021803 A1 | 9/2001 | Blank et al. |
| 2001/0039376 A1 | 11/2001 | Steuer et al. |
| 2001/0044700 A1 | 11/2001 | Kobayashi et al. |
| 2001/0051767 A1 | 12/2001 | Williams et al. |
| 2002/0026106 A1 | 2/2002 | Khalil et al. |
| 2002/0026109 A1 | 2/2002 | Diab et al. |
| 2002/0028990 A1 | 3/2002 | Shepherd et al. |
| 2002/0035318 A1 | 3/2002 | Mannheimer et al. |
| 2002/0038078 A1 | 3/2002 | Ito |
| 2002/0038079 A1 | 3/2002 | Steuer et al. |
| 2002/0042558 A1 | 4/2002 | Mendelson |
| 2002/0049389 A1 | 4/2002 | Abreu |
| 2002/0062071 A1 | 5/2002 | Diab et al. |
| 2002/0068859 A1 | 6/2002 | Knopp |
| 2002/0111748 A1 | 8/2002 | Kobayashi et al. |
| 2002/0128544 A1 | 9/2002 | Diab et al. |
| 2002/0133067 A1 | 9/2002 | Jackson, III |
| 2002/0133068 A1 | 9/2002 | Huiku |
| 2002/0156354 A1 | 10/2002 | Larson |
| 2002/0161287 A1 | 10/2002 | Schmitt |
| 2002/0161290 A1 | 10/2002 | Chance |
| 2002/0165439 A1 | 11/2002 | Schmitt |
| 2002/0173706 A1 | 11/2002 | Takatani |
| 2002/0173709 A1 | 11/2002 | Fine et al. |
| 2002/0190863 A1 | 12/2002 | Lynn |
| 2002/0198442 A1 | 12/2002 | Rantala et al. |
| 2002/0198443 A1 | 12/2002 | Ting |
| 2003/0018243 A1 | 1/2003 | Gerhardt et al. |
| 2003/0023140 A1 | 1/2003 | Chance |

| | | |
|---|---|---|
| 2003/0036690 A1 | 2/2003 | Geddes et al. |
| 2003/0045785 A1 | 3/2003 | Diab et al. |
| 2003/0055324 A1 | 3/2003 | Wasserman |
| 2003/0060693 A1 | 3/2003 | Monfre et al. |
| 2003/0073889 A1 | 4/2003 | Keilbach et al. |
| 2003/0073890 A1 | 4/2003 | Hanna |
| 2003/0100840 A1 | 5/2003 | Sugiura et al. |
| 2003/0132495 A1 | 7/2003 | Mills et al. |
| 2003/0135099 A1 | 7/2003 | Al-Ali |
| 2003/0139687 A1 | 7/2003 | Abreu |
| 2003/0144584 A1 | 7/2003 | Mendelson |
| 2003/0162414 A1 | 8/2003 | Schulz et al. |
| 2003/0171662 A1 | 9/2003 | O'Connor et al. |
| 2003/0176776 A1 | 9/2003 | Huiku |
| 2003/0181799 A1 | 9/2003 | Lindekugel et al. |
| 2003/0187337 A1 | 10/2003 | Tarassenko et al. |
| 2003/0195402 A1 | 10/2003 | Fein et al. |
| 2003/0197679 A1 | 10/2003 | Ali et al. |
| 2003/0212316 A1 | 11/2003 | Leiden et al. |
| 2003/0220548 A1 | 11/2003 | Schmitt |
| 2003/0220576 A1 | 11/2003 | Diab |
| 2003/0225323 A1 | 12/2003 | Kiani et al. |
| 2003/0225337 A1 | 12/2003 | Scharf et al. |
| 2003/0236452 A1 | 12/2003 | Melker et al. |
| 2003/0236647 A1 | 12/2003 | Yoon et al. |
| 2004/0006261 A1 | 1/2004 | Swedlow et al. |
| 2004/0010188 A1 | 1/2004 | Wasserman |
| 2004/0024297 A1 | 2/2004 | Chen et al. |
| 2004/0024326 A1 | 2/2004 | Yeo et al. |
| 2004/0034293 A1 | 2/2004 | Kimball |
| 2004/0039272 A1 | 2/2004 | Abdul-Hafiz et al. |
| 2004/0039273 A1 | 2/2004 | Terry |
| 2004/0054269 A1 | 3/2004 | Rantala et al. |
| 2004/0054291 A1 | 3/2004 | Schulz et al. |
| 2004/0059209 A1 | 3/2004 | Al-Ali et al. |
| 2004/0059210 A1 | 3/2004 | Stetson |
| 2004/0064020 A1 | 4/2004 | Diab et al. |
| 2004/0068164 A1 | 4/2004 | Diab et al. |
| 2004/0087846 A1 | 5/2004 | Wasserman |
| 2004/0092805 A1 | 5/2004 | Yarita |
| 2004/0097797 A1 | 5/2004 | Porges et al. |
| 2004/0098009 A1 | 5/2004 | Boecker et al. |
| 2004/0107065 A1 | 6/2004 | Al-Ali et al. |
| 2004/0116788 A1 | 6/2004 | Chernoguz et al. |
| 2004/0116789 A1 | 6/2004 | Boaz et al. |
| 2004/0117891 A1 | 6/2004 | Hannula et al. |
| 2004/0122300 A1 | 6/2004 | Boas et al. |
| 2004/0122302 A1 | 6/2004 | Mason et al. |
| 2004/0127779 A1 | 7/2004 | Steuer et al. |
| 2004/0133087 A1 | 7/2004 | Ali et al. |
| 2004/0133088 A1 | 7/2004 | Al-Ali et al. |
| 2004/0138538 A1 | 7/2004 | Stetson |
| 2004/0138540 A1 | 7/2004 | Baker, Jr. et al. |
| 2004/0143172 A1 | 7/2004 | Fudge et al. |
| 2004/0147821 A1 | 7/2004 | Al-Ali et al. |
| 2004/0147822 A1 | 7/2004 | Al-Ali et al. |
| 2004/0147823 A1 | 7/2004 | Kiani et al. |
| 2004/0147824 A1 | 7/2004 | Diab et al. |
| 2004/0152965 A1 | 8/2004 | Diab et al. |
| 2004/0158134 A1 | 8/2004 | Diab et al. |
| 2004/0158135 A1 | 8/2004 | Baker, Jr. et al. |
| 2004/0162472 A1 | 8/2004 | Berson et al. |
| 2004/0171920 A1 | 9/2004 | Mannheimer et al. |
| 2004/0171948 A1 | 9/2004 | Terry |
| 2004/0176670 A1 | 9/2004 | Takamura et al. |
| 2004/0176671 A1 | 9/2004 | Fine et al. |
| 2004/0181133 A1 | 9/2004 | Al-Ali |
| 2004/0181134 A1 | 9/2004 | Baker, Jr. et al. |
| 2004/0186358 A1 | 9/2004 | Chernow et al. |
| 2004/0199063 A1 | 10/2004 | O'Neil et al. |
| 2004/0204636 A1 | 10/2004 | Diab et al. |
| 2004/0204637 A1 | 10/2004 | Diab et al. |
| 2004/0204638 A1 | 10/2004 | Diab et al. |
| 2004/0204639 A1 | 10/2004 | Casciani et al. |
| 2004/0204865 A1 | 10/2004 | Lee et al. |
| 2004/0210146 A1 | 10/2004 | Diab et al. |
| 2004/0215069 A1 | 10/2004 | Mannheimer |
| 2004/0230106 A1 | 11/2004 | Schmitt et al. |
| 2004/0230107 A1 | 11/2004 | Asada et al. |
| 2004/0230108 A1 | 11/2004 | Melker et al. |
| 2004/0236196 A1 | 11/2004 | Diab et al. |
| 2004/0242980 A1 | 12/2004 | Kiani et al. |
| 2004/0249252 A1 | 12/2004 | Fine et al. |
| 2004/0257557 A1 | 12/2004 | Block et al. |
| 2004/0260161 A1 | 12/2004 | Melker et al. |
| 2004/0267103 A1 | 12/2004 | Li et al. |
| 2004/0267104 A1 | 12/2004 | Hannula et al. |
| 2004/0267140 A1 | 12/2004 | Ito et al. |
| 2005/0004479 A1 | 1/2005 | Townsend et al. |
| 2005/0010092 A1 | 1/2005 | Weber et al. |
| 2005/0020887 A1 | 1/2005 | Goldberg |
| 2005/0020894 A1 | 1/2005 | Norris et al. |
| 2005/0033128 A1 | 2/2005 | Ali et al. |
| 2005/0033129 A1 | 2/2005 | Edgar, Jr. et al. |
| 2005/0043599 A1 | 2/2005 | O'Mara |
| 2005/0043600 A1 | 2/2005 | Diab et al. |
| 2005/0049470 A1 | 3/2005 | Terry |
| 2005/0049471 A1 | 3/2005 | Aceti |
| 2005/0075550 A1 | 4/2005 | Lindekugel |
| 2005/0080323 A1 | 4/2005 | Kato |
| 2005/0101850 A1 | 5/2005 | Parker |
| 2005/0113651 A1 | 5/2005 | Wood et al. |
| 2005/0113656 A1 | 5/2005 | Chance |
| 2005/0168722 A1 | 8/2005 | Forstner et al. |
| 2005/0177034 A1 | 8/2005 | Beaumont |
| 2005/0192488 A1 | 9/2005 | Bryenton |
| 2005/0197548 A1 | 9/2005 | Dietiker |
| 2005/0203357 A1 | 9/2005 | Debreczeny |
| 2005/0228248 A1 | 10/2005 | Dietiker |
| 2005/0267346 A1 | 12/2005 | Faber et al. |
| 2005/0277819 A1 | 12/2005 | Kiani et al. |
| 2005/0283059 A1 | 12/2005 | Iyer et al. |
| 2006/0009688 A1 | 1/2006 | Lamego et al. |
| 2006/0015021 A1 | 1/2006 | Cheng |
| 2006/0020181 A1 | 1/2006 | Schmitt |
| 2006/0030763 A1 | 2/2006 | Mannheimer et al. |
| 2006/0052680 A1 | 3/2006 | Diab |
| 2006/0058594 A1 | 3/2006 | Ishizuka et al. |
| 2006/0058683 A1 | 3/2006 | Chance |
| 2006/0064024 A1 | 3/2006 | Schnall |
| 2006/0084852 A1 | 4/2006 | Mason et al. |
| 2006/0089547 A1 | 4/2006 | Sarussi |
| 2006/0106294 A1 | 5/2006 | Maser et al. |
| 2006/0195028 A1 | 8/2006 | Hannula et al. |
| 2006/0224053 A1 | 10/2006 | Black et al. |
| 2006/0224058 A1 | 10/2006 | Mannheimer |
| 2006/0247501 A1 | 11/2006 | Ali |
| 2006/0253007 A1 | 11/2006 | Cheng et al. |
| 2006/0258921 A1 | 11/2006 | Addison et al. |
| 2006/0276700 A1 | 12/2006 | O'Neil |
| 2007/0032710 A1 | 2/2007 | Raridan et al. |
| 2007/0032712 A1 | 2/2007 | Raridan et al. |
| 2007/0032715 A1 | 2/2007 | Eghbal et al. |
| 2007/0049811 A1 | 3/2007 | Kobayashi et al. |
| 2007/0073121 A1 | 3/2007 | Hoarau et al. |
| 2007/0073125 A1 | 3/2007 | Hoarau et al. |
| 2007/0073126 A1 | 3/2007 | Raridan, Jr. |
| 2007/0073128 A1 | 3/2007 | Hoarau et al. |
| 2007/0260132 A1 | 11/2007 | Sterling |
| 2008/0117616 A1 | 5/2008 | Coakley |
| 2009/0171175 A1 | 7/2009 | Li et al. |

FOREIGN PATENT DOCUMENTS

| | | |
|---|---|---|
| DE | 19647877 | 5/1998 |
| EP | 0615723 | 9/1994 |
| EP | 0702931 | 3/1996 |
| EP | 0724860 | 8/1996 |
| EP | 1332713 | 8/2003 |
| EP | 1491135 | 12/2004 |
| FR | 2685865 | 7/1993 |
| JP | 63275325 | 11/1988 |
| JP | 3124073 | 5/1991 |
| JP | 3170866 | 7/1991 |
| JP | 3238813 | 10/1991 |
| JP | 3245042 | 10/1991 |
| JP | 4332536 | 11/1992 |
| JP | 5049624 | 3/1993 |
| JP | 6154177 | 6/1994 |

| | | |
|---|---|---|
| JP | 6269430 | 9/1994 |
| JP | 6285048 | 10/1994 |
| JP | 7001273 | 1/1995 |
| JP | 7124138 | 5/1995 |
| JP | 7136150 | 5/1995 |
| JP | 2003194714 | 7/2003 |
| JP | 2003210438 | 7/2003 |
| JP | 2004194908 | 7/2004 |
| JP | 2004248819 | 9/2004 |
| JP | 2004261364 | 9/2004 |
| JP | 2004290545 | 10/2004 |
| JP | 2005034472 | 2/2005 |
| WO | WO8909566 | 10/1989 |
| WO | WO9001293 | 2/1990 |
| WO | WO9101678 | 2/1991 |
| WO | WO9111137 | 8/1991 |
| WO | WO9200513 | 1/1992 |
| WO | WO9309711 | 5/1993 |
| WO | WO9316629 | 9/1993 |
| WO | WO9423643 | 10/1994 |
| WO | WO9502358 | 1/1995 |
| WO | WO9639927 | 12/1996 |
| WO | WO9932030 | 7/1999 |
| WO | WO0021438 | 4/2000 |
| WO | WO0028888 | 5/2000 |
| WO | WO0140776 | 6/2001 |
| WO | WO0176461 | 10/2001 |
| WO | WO0176471 | 10/2001 |
| WO | WO03039326 | 5/2003 |
| WO | WO2005065540 | 7/2005 |
| WO | WO2008039195 | 4/2008 |

OTHER PUBLICATIONS

Barnum, P.T., et al.; "Novel Pulse Oximetry Technology Capable of Reliable Bradycardia Monitoring in the Neonate," Respiratory Care, vol. 42, No. 1, p. 1072 (Nov. 1997).

Barreto, Armando B., et al.; "Adaptive LMS Delay Measurement in dual Blood Volume Pulse Signals for Non-Invasive Monitoring," IEEE, pp. 117-120 (1997).

Buschman, J.P., et al.; "Principles and Problems of Calibration of Fetal Oximeters," Biomedizinische Technik, vol. 42, pp. 265-266 (1997).

Leahy, Martin J., et al.; "Sensor Validation in Biomedical Applications," IFAC Modelling and Control in Biomedical Systems, Warwick, UK; pp. 221-226 (1997).

Pickett, John, et al.; "Pulse Oximetry and PPG Measurements in Plastic Surgery," Proceedings—19th International Conference—IEEE/EMBS, Chicago, Illinois, Oct. 30-Nov. 2, 1997, pp. 2330-2332.

East, Christine E., et al.; "Fetal Oxygen Saturation and Uterine Contractions During Labor," American Journal of Perinatology, vol. 15, No. 6, pp. 345-349 (Jun. 1998).

Edrich, Thomas, et al.; "Can the Blood Content of the Tissues be Determined Optically During Pulse Oximetry Without Knowledge of the Oxygen Saturation?—An In-Vitro Investigation," Proceedings of the 20th Annual International conference of the IEEE Engie in Medicine and Biology Society, vol. 20, No. 6, p. 3072-3075, 1998.

Such, Hans Olaf; "Optoelectronic Non-invasive Vascular Diagnostics Using multiple Wavelength and Imaging Approach," Dissertation, (1998).

Lutter, N., et al.; "Comparison of Different Evaluation Methods for a Multi-wavelength Pulse Oximeter," Biomedizinische Technik, vol. 43, (1998).

Ikeda, Kenji, et al.; "Improvement of Photo-Electric Plethysmograph Applying Newly Developed Opto-Electronic Devices," IEEE Tencon, pp. 1109-1112 (1999).

Todd, Bryan, et al.; "The Identification of Peaks in Physiological Signals," Computers and Biomedical Research, vol. 32, pp. 322-335 (1999).

Seelbach-Göbel, Birgit, et al.; "The prediction of fetal acidosis by means of intrapartum fetal pulse oximetry," Am J. Obstet. Gynecol., vol. 180, No. 1, Part 1, pp. 73-81 (1999).

Goldman, Julian M.; "Masimo Signal Extraction Pulse Oximetry," Journal of Clinical Monitoring and Computing, vol. 16, pp. 475-483 (2000).

Coetzee, Frans M.; "Noise-Resistant Pulse Oximetry Using a Synthetic Reference Signal," IEEE Transactions on Biomedical Engineering, vol. 47, No. 8, Aug. 2000, pp. 1018-1026.

Nilsson, Lena, et al.; "Monitoring of Respiratory Rate in Postoperative Care Using a New Photoplethysmographic Technique," Journal of Clinical Monitoring and Computing, vol. 16, pp. 309-315 (2000).

Kaestle, S.; "Determining Artefact Sensitivity of New Pulse Oximeters in Laboratory Using Signals Obtained from Patient," Biomedizinische Technik, vol. 45 (2000).

Belal, Suliman Yousef, et al.; "A fuzzy system for detecting distorted plethysmogram pulses in neonates and paediatric patients," Physiol. Meas., vol. 22, pp. 397-412 (2001).

Cubeddu, Rinaldo, et al.; "Portable 8-channel time-resolved optical imager for functional studies of biological tissues," Photon Migration, Optical Coherence Tomography, and Microscopy, Proceedings of SPIE, vol. 4431, pp. 260-265 (2001).

Cysewska-Sobusaik, Anna; "Metrological Problems With noninvasive Transillumination of Living Tissues," Proceedings of SPIE, vol. 4515, pp. 15-24 (2001).

Lopez-Silva, Sonnia Maria Lopez, et al.; "NIR transmittance pulse oximetry system with laser diodes," Clinical Diagnostic Systems, Proceedings of SPIE, vol. 4255, pp. 80-87 (2001).

Maletras, Francois-Xavier, et al.; "Construction and calibration of a new design of Fiber Optic Respiratory Plethysmograph (FORP)," Optomechanical Design and Engineering, Proceedings of SPIE, vol. 4444, pp. 285-293 (2001).

Earthrowl-Gould, T., et al.; "Chest and abdominal surface motion measurement for continuous monitoring of respiratory function," Proc. Instn Mech Engrs, V215, Part H; pp. 515-520 (2001).

Relente, A.R., et al.; "Characterization and Adaptive Filtering of Motion Artifacts in Pulse Oximetry using Accelerometers," Proceedings of the Second joint EMBS/BMES Conference, Houston, Texas, Oct. 23-26, 2002; pp. 1769-1770.

Liu, Ying, et al.; "Sensor design of new type reflectance pulse oximetry," Optics in Health Care and Biomedical Optics: Diagnostics and Treatment, Proceedings of SPIE, vol. 4916, pp. 98-102 (2002).

Chan, K.W., et al.; "17.3: Adaptive Reduction of Motion Artifact from Photoplethysmographic Recordings using a Variable Step-Size LMS Filter," IEEE, pp. 1343-1346 (2002).

Yao, Jianchu, et al.; "Design of a Plug-and-Play Pulse Oximeter," Proceedings of the Second Joint EMBS/BMES Conference, Houston, Texas, Oct. 23-26, 2002; pp. 1752-1753.

Yoon, Gilwon, et al.; "Multiple diagnosis based on Photoplethysmography: hematocrit, SpO2, pulse and respiration," Optics in Health Care and Biomedical optics: Diagnostics and Treatment; Proceedings of the SPIE, vol. 4916; pp. 185-188 (2002).

Lopez-Silva, Sonnia Maria Lopez, et al.; "Near-infrared transmittance pulse oximetry with laser diodes," Journal of Biomedical Optics, vol. 8, No. 3, pp. 525-533 (Jul. 2003).

Cyrill, D., et al.; "Adaptive Comb Filter for Quasi-Periodic Physiologic Signals," Proceedings of the 25th Annual International Conference of the IEEE EMBS, Cancun, Mexico, Sep. 17-21, 2003; pp. 2439-2442.

Matthews, Nora S. et al.; "An evaluation of pulse oximeters in dogs, cats and horses," Veterinary Anaesthesia and Analgesia, vol. 30, pp. 3-14 (2003).

Stetson, Paul F.; "Determining Heart Rate from Noisey Pulse Oximeter Signals Using Fuzzy Logic," The IEEE International Conference on Fuzzy Systems, St. Louis, Missouri, May 25-28, 2003; pp. 1053-1058.

Pujary, C., et al.; "Photodetector Size Considerations in the Design of a Noninvasive Reflectance Pulse Oximeter for Telemedicine Applications," IEEE, pp. 148-149 (2003).

Lee, C.M., et al.; "Reduction of motion artifacts from photoplethysmographic recordings using wavelet denoising approach," IEEE EMBS Asian-Pacific Conference on Biomedical Engineering, Oct. 20-22, 2003; pp. 194-195.

Johnston, W.S., et al.; "Extracting Breathing Rate Infromation from a Wearable Reflectance Pulse Oximeter Sensor," *Proceedings of the 26th Annual International conference of the IEEE EMBS*, San Francisco, California; Sep. 1-5, 2004; pp. 5388-5391.

Spigulis, Janis, et al.; "Optical multi-channel sensing of skin blood pulsations," Optical Sensing, *Proceedings of SPIE*, vol. 5459, pp. 46-53 (2004).

Lutter, N., et al.; "Accuracy of Noninvasive Continuous Blood Pressure; Measurement Utilising the Pulse Transit Time," *Journal of clinical Monitoring and Computing*, vol. 17, Nos. 7-8, pp. 469 (2002).

A. Johansson; "Neural network for photoplethysmographic respiratory rate monitoring," *Medical & Biological Engineering & Computing*, vol. 41, pp. 242-248 (2003).

Lopez-Silva, S.M., et al.; "Transmittance Photoplethysmography and Pulse Oximetry With Near Infrared Laser Diodes," *IMTC 2004—Instrumentation and Measurement Technology Conference*, Como, Italy, May 18-20, 2004; pp. 718-723.

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

METHOD AND APPARATUS FOR DETECTING AND ANALYZING VARIATIONS IN A PHYSIOLOGIC PARAMETER

BACKGROUND

The present disclosure relates generally to identifying and/or analyzing variations in a measured physiologic parameter, such as blood oxygen saturation ($SpO_2$) measured using pulse oximetry. More particularly, the present disclosure includes embodiments directed to analyzing variations in $SpO_2$ values and/or variations in $SpO_2$ trend data that are smaller in magnitude than the accuracy, display precision, and/or calibration of the measurement.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Pulse oximetry is used to continuously monitor the oxygen content of patients' blood in various settings (e.g., operating rooms, delivery rooms, and so forth). Specifically, pulse oximetry uses light waves to indirectly measure the arterial blood oxygen saturation of patients. For example, in operation, conventional two wavelength pulse oximeters emit light from two emitters (e.g., light emitting diodes (LEDs)) into a pulsatile tissue bed and collect the transmitted light with a detector (e.g., a photodiode). The detected light may then be utilized to estimate a level of oxygen saturation in the blood that is present in the tissue bed. The emitters and detector may be positioned in various orientations for different types of pulse oximetry. For example, in transmission pulse oximetry, the emitters and detector are positioned substantially opposite one another (e.g., on opposite sides of a patient's finger), while in reflectance pulse oximetry, the emitters and detector are placed adjacent to one another. The emitters and detector are typically housed in a sensor which connects to pulse oximeter electronics.

The "pulse" in pulse oximetry comes from the time varying amount of arterial blood in the tissue bed during the cardiac cycle. The processed signals from the photodetector create the familiar plethysmographic waveform due to the cycling light attenuation caused by the varying amount of arterial blood that the light from the emitters passes through. With regard to conventional two-wavelength pulse oximeters, at least one of two LEDs emits light at a wavelength at some point in the electromagnetic spectrum where the absorption of oxyhemoglobin ($O_2Hb$) differs from the absorption of reduced hemoglobin (HHb), and the other of the two LEDs emits light at a wavelength that is at a different point in the spectrum where the absorption differences between HHb and $O_2Hb$ are different from those at the first wavelength. The use of these differing wavelengths facilitates estimation of blood oxygen saturation.

Typically, pulse oximeters utilize one wavelength in the red part of the visible spectrum near 660 nanometers (nm), and one in the near infrared part of the spectrum in the range of 880 nm-940 nm. Photocurrents generated within the detector are detected and processed for measuring the modulation ratio of the red to infrared signals. This modulation ratio has been observed to correlate well to arterial oxygen saturation. Pulse oximeters and pulse oximetry sensors are empirically calibrated by measuring the modulation ratio over a range of in vivo measured arterial oxygen saturations ($SaO_2$) on a set of patients, healthy volunteers, or animals. The observed correlation is used in an inverse manner to determine $SpO_2$ based on the real-time measured value of modulation ratios. It should be noted that, as used herein, $SaO_2$ refers to the in vivo measured functional saturation, while $SpO_2$ refers to the estimated functional saturation using pulse oximetry.

Traditional uses of pulse oximetry are based on rounded values of $SpO_2$. Indeed, because $SpO_2$ values are generally only accurate to about 1 or 2%, the $SpO_2$ values are typically used after they have been rounded to the nearest 1%. Further, traditional uses of pulse oximetry may not typically benefit from more precise calculation. For example, pulse oximetry has traditionally been used on patient populations where arterial blood oxygen saturation is generally greater than 90%. In other words, pulse oximetry has traditionally been used in patient populations, wherein the functional hemoglobin in the arterial blood includes at least 90% oxyhemoglobin and 10% or less reduced hemoglobin. In such patient populations, oxygen saturation seldom falls below 80%, and such low values are generally indicative of an unhealthy condition that warrants intervention. Thus, in this and similar situations where pulse oximetry has typically been employed, a high degree of precision in the estimate of blood oxygen saturation based on traditional pulse oximetry has not generally been considered to be clinically relevant.

BRIEF DESCRIPTION OF THE DRAWINGS

Advantages of the present disclosure may become apparent upon reading the following detailed description and upon reference to the drawings in which.

DETAILED DESCRIPTION OF SPECIFIC EMBODIMENTS

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover; it should be appreciated that such a development effort might be complex and time consuming, but would nevertheless be a routine undertaking of design, fabrication, and manufacture for those of ordinary skill having the benefit of this disclosure.

Present embodiments may be applied in the field of pulse oximetry. As indicated above, pulse oximetry may be defined as a non-invasive technique that facilitates monitoring of a patient's blood characteristics. For example, pulse oximetry may be used to measure blood oxygen saturation of hemoglobin in a patient's arterial blood and/or the patient's heart rate. Specifically, these measurements may be acquired using a non-invasive sensor that passes light through a portion of a patient's tissue and photo-electrically senses the absorption and scattering of the light through the tissue. Typical pulse oximetry technology currently utilizes two LEDs and a single optical detector to measure pulse and oxygen saturation of a given tissue bed. Such measurements are largely based on absorption of emitted light by specific types of blood constituents. Once acquired, this measurement may be used with various algorithms to estimate a relative amount of blood constituent in the tissue. For example, such measurements may provide a ratio of oxygenated to the sum of oxygenated and deoxygenated hemoglobin (i.e., functional hemoglobin) in the volume being monitored.

An $SpO_2$ value is generally considered to be limited in accuracy to within a few percentage points relative to invasively measured values of $SaO_2$. Thus, traditional pulse oximeters do not typically display $SpO_2$ values that have a greater precision than one percent. Likewise, traditional pulse oximeter systems do not perform control functions based on such precise values. It should be noted that the term "accurate" generally refers to a degree of correctness (i.e., closeness to a true value), while the term "precise" generally refers to a degree of exactness, that is, to the smallest change that can be detected in a value.

It has now been recognized that trending accuracy of high precision $SpO_2$ values is substantially more accurate than the individual values of $SpO_2$. In other words, the changes or differences between calculated $SpO_2$ values have been found to correspond closely with corresponding changes in values of $SaO_2$. Thus, changes in $SpO_2$ at high levels of precision are now recognized as accurate representations of changes in $SaO_2$. Accordingly, present embodiments are directed to systems and methods for analyzing variations in a measured physiologic parameter, such as $SpO_2$, where the variations are smaller in magnitude than the measurement's accuracy or display precision, or where the measurements are outside the displayed or calibrated range of the measured physiologic parameter. For example, $SpO_2$ values may only be accurate to within a range of +/−1 or 2% relative to an actual value of $SaO_2$. However, in present embodiments, $SpO_2$ values may be determined at a high resolution (e.g., a precision of 0.1%, 0.01%, or 0.001%) for use in pattern detection calculations, control algorithms, and so forth. Indeed, present embodiments may not round to the nearest 1%, which may increase the accuracy in detected changes in $SpO_2$. Similarly, while a pulse oximeter may only display $SpO_2$ values with limited precision (e.g., only whole number percentage values) and/or $SpO_2$ values within the range of 0-100%, present embodiments may utilize high resolution $SpO_2$ values and $SpO_2$ values outside the range of 0-100% to facilitate analysis, control, and treatment based on subtle changes in the high resolution $SpO_2$ values over time.

Specifically, present embodiments may utilize subtle variations in high resolution $SpO_2$ values, such as an incremental variation in the tenths, hundredths, or thousandths digit of an $SpO_2$ value, to detect or compensate for more significant variations in a related physiologic parameter. For example, small changes in an $SpO_2$ value may correspond to significant changes in minute ventilation, respiration rate, apnea, partial pressure of oxygen in the arterial blood and so forth. Thus, in accordance with present embodiments, subtle changes in high resolution $SpO_2$ values detected over time may be utilized to analyze and/or control variations in minute ventilation, respiration rate, partial pressure of oxygen in the arterial blood and/or apnea (e.g., obstructive sleep apnea or central sleep apnea). Further, present embodiments may include features for tracking subtle changes in $SpO_2$ and presenting them as changes in a related parameter based on the use of the $SpO_2$ values as a surrogate.

Further, present embodiments may facilitate detection, analysis, and/or control of physiologic parameters based on high resolution $SpO_2$ values by utilizing and/or including a sensor that is capable of enhancing measurement precision. For example, present embodiments may include an $SpO_2$ sensor with an emitter that functions to emit light at one or more wavelengths that facilitate increased sensitivity. Such sensitivity may further enable detection of high precision changes in $SpO_2$ values by a processor of the sensor, which can be utilized for control, detection, and so forth in accordance with present embodiments. It is now recognized based on calculations directed to increasing the slope of a modulation ratio versus $SaO_2$ curve, that the relative change or percentage difference in HHb to $O_2$Hb of a pair of signals facilitates high resolution determination of $SpO_2$ values. Specifically, for example, an $SpO_2$ sensor in accordance with present embodiments may include emitters with wavelengths near 660 nm (e.g., 650-670 nm) and near 950 nm (e.g., 940-1000 nm), as these two wavelengths may exhibit the greatest relative differences in absorbance from HHb and $O_2$Hb and, as a result, provide improved $SpO_2$ precision. It may be desirable to use a wavelength of 950 nm because silicon detectors generally roll off after around 950 nm. In some embodiments, green or yellow light may be utilized separately or in combination with the sensor's others LEDs. For example, a green LED that produces light with a wavelength in a range of about 500-570 nm or a yellow LED that produces light with a wavelength in a range of about 570-600 nm may be utilized in accordance with present embodiments because the wavelengths are typically more highly absorbed by hemoglobin, and may therefore enable the acquisition of a stronger pulsatile signal that facilicates detection of smaller changes in $SpO_2$.

Additionally, the spacing used between the emitter and detector in a reflectance sensor may be chosen to increase the precision of $SpO_2$ calculations. With a narrow spacing between the emitter and detector, the change in the pulse oximeter's modulation ratio for a given change in $SaO_2$ is larger than is found with a less narrow spacing. For example, a sensor with a 2-mm spacing between the LED light sources and the photodetector provides an improved precision in the $SpO_2$ estimate of $SaO_2$ relative to a sensor with a 10-mm spacing. Accordingly, present embodiments may utilize a spacing of approximately 2-3 mm between the LED light sources to generate high resolution values.

Figure 1:
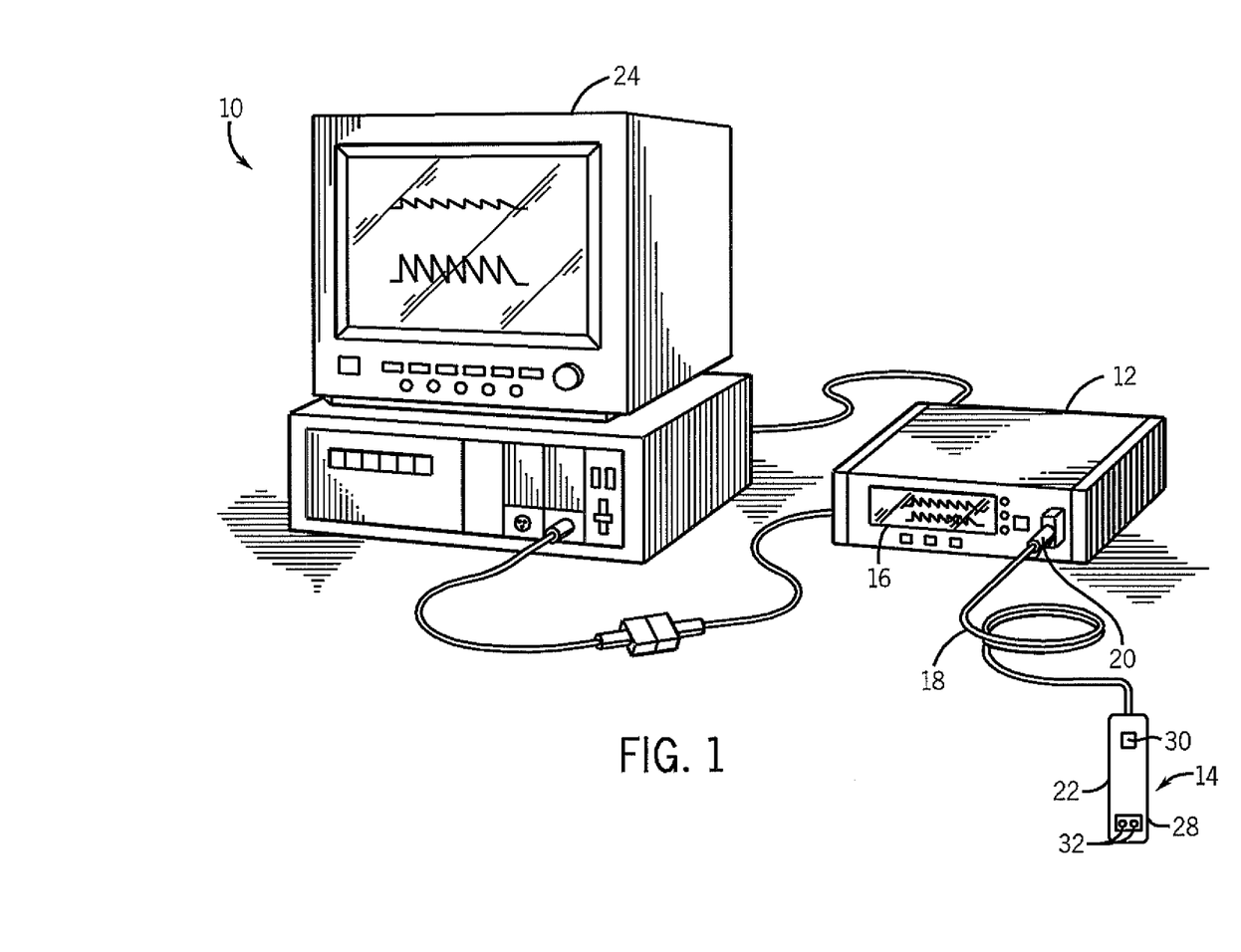
FIG. 1 is a perspective view of a pulse oximeter system in accordance with an embodiment.

FIG. 1 illustrates a perspective view of a pulse oximetry system 10 in accordance with present embodiments. The system 10 may be utilized to observe the blood constituents of a patient's arterial blood to facilitate estimation of the state of oxygen exchange in the patient's body by emitting waves into tissue and detecting the waves after dispersion and/or reflection by the tissue. The system 10 may include a pulse oximeter or monitor 12 that communicatively couples to a sensor 14. The monitor 12 may include a display 16, a memory, a processor, and various monitoring and control features. The monitor 12 may be configured to perform pulse oximetry measurements, calculations, and control algorithms using high precision values in accordance with present embodiments. Further, the monitor 12 may be configured to display high resolution $SpO_2$ values based on the measurements, calculations, and control algorithms. The sensor 14 may include a sensor cable 18, a connector plug 20, and a sensor assembly or body 22 configured to attach to a patient (e.g., a patient's finger, ear, forehead, or toe). Further, in the illustrated embodiment, the system 10 includes a separate display feature 24 that is communicatively coupled with the monitor 12 to facilitate presentation of pulse oximetry data and related data.

The sensor 14 includes an emitter 28 and a detector 30. When attached to a patient's tissue and functioning, the emitter 28 transmits light at different wavelengths into the tissue and the detector 30 receives the light after it has passed through the tissue area. The amount of light that passes through the tissue and other characteristics of light waves may vary in accordance with the changing amount of certain blood constituents in the tissue and the related light absorption and/or scattering. For example, the system 10 may emit light from two or more LEDs 32, or other suitable light sources such as lasers, into the pulsatile tissue and then detect the transmitted light with the detector 30, such as a photodiode or photo-detector, after the light has passed through the pulsatile tissue. Such measurements may be utilized to estimate a percentage of blood oxygen saturation in the probed volume of blood. In other words, such measurements may be utilized to obtain an $SpO_2$ value. Further, such measurements may be utilized to track related parameters. For example, $SpO_2$ measurements may be utilized to track the partial pressure of oxygen ($pO_2$) in a patient's arterial blood by relating the $pO_2$ to the $SpO_2$ through the use of a selected or calculated oxygen dissociation curve. Indeed, $SpO_2$ may be utilized as a surrogate for $pO_2$.

Figure 2:
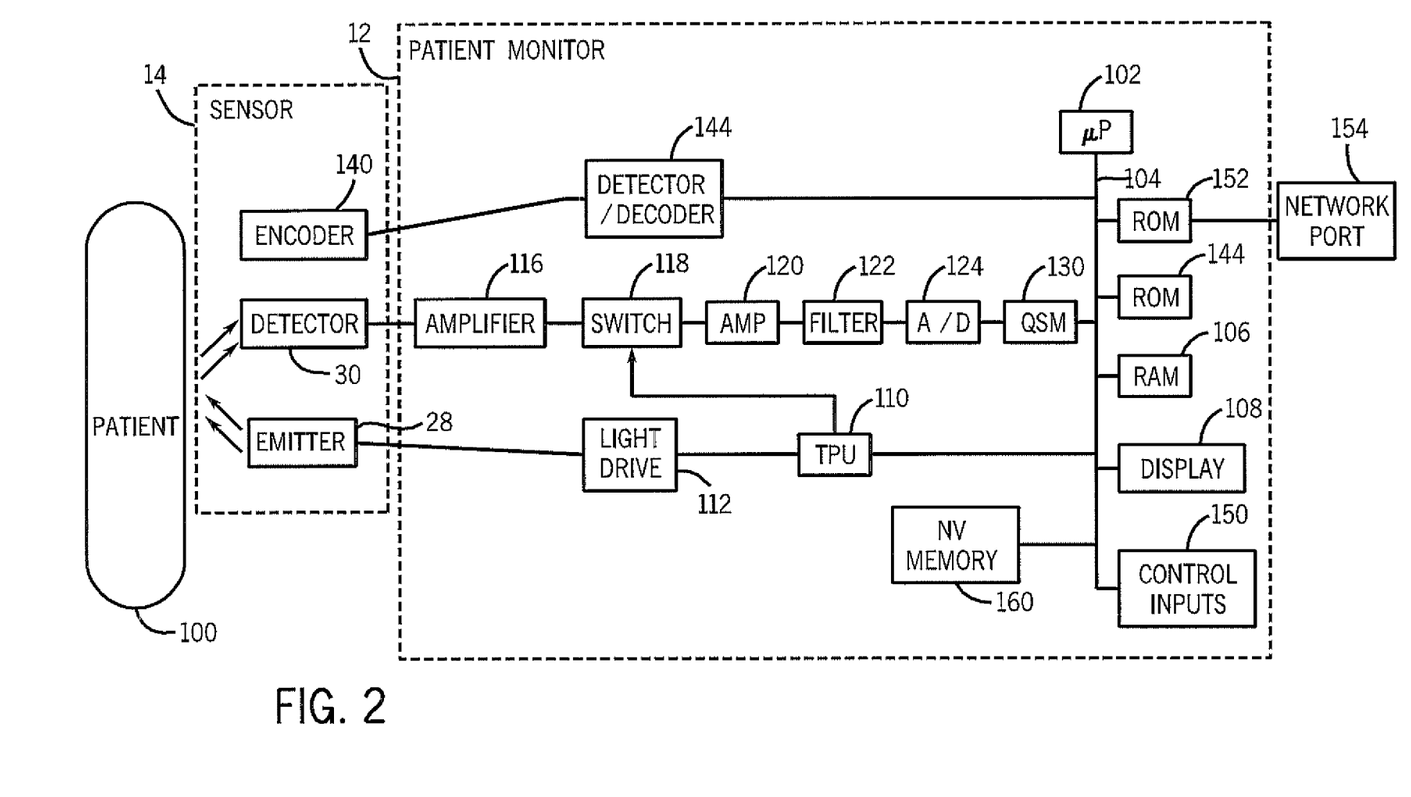
FIG. 2 is a block diagram of a pulse oximeter system in accordance with an embodiment.

FIG. 2 is a block diagram of an embodiment of the patient monitoring system 10 that may be configured to implement the techniques described herein. The system 10 may include the patient monitor 12 (e.g., a pulse oximeter) and the sensor 14, which are configured to obtain and utilized high precision $SpO_2$ values. The sensor 14 is communicatively connected to the patient monitor 12 via a cable or wireless device. When the system 10 is operating, light from the emitter 28 may pass into a patient 100 and be scattered and detected by the detector 30. The monitor 12 may include a microprocessor 102 connected to an internal bus 104. Also connected to the bus 104 may be a RAM memory 106 and a display 108. A time processing unit (TPU) 110 may provide timing control signals to light drive circuitry 112 which may control when the emitter 28 is illuminated, and if multiple light sources are used, the multiplexed timing for the different light sources. TPU 110 may also control the gating-in of signals from the detector 30 through an amplifier 116 and a switching circuit 118. These signals may be sampled at the proper time, depending upon which of multiple light sources is illuminated, if multiple light sources are used. The received signal from the detector 30 may be passed through an amplifier 120, a low pass filter 122, and an analog-to-digital converter 124. The digital data may then be stored in a queued serial module (QSM) 130, for later downloading to the RAM 106 as the QSM 130 fills up. In one embodiment, there may be multiple parallel paths of separate amplifier, filter and A/D converters for multiple light wavelengths or spectra received. It should be noted that each of these features may be configured to facilitate the provision of $SpO_2$ values at a high level of precision in accordance with present embodiments. Present embodiments may be implemented on any suitable pulse oximeter, such as those available from Nellcor Puritan Bennett LLC.

In an embodiment, the sensor 14 may also contain an encoder 140 that provides signals indicative of the wavelength of one or more light sources of the emitter 28 to allow the monitor 12 to select appropriate calibration coefficients for calculating a physiological parameter such as blood oxygen saturation. The encoder 140 may, for instance, be a coded resistor, EEPROM or other coding devices (such as a capacitor, inductor, PROM, RFID, a barcode, parallel resonant circuits, or a colorimetric indicator) that may provide a signal to the processor 102 related to the characteristics of the sensor 14 that may allow the processor 102 to determine the appropriate calibration characteristics for the sensor 14. Further, the encoder 140 may include encryption coding that prevents a disposable part of the sensor 14 from being recognized by a processor 102 that is not able to decode the encryption. For example, a detector/decoder 144 may be required to translate information from the encoder 140 before it can be properly handled by the processor 102. Present embodiments may be implemented on any suitable sensor, such as those available from Nellcor Puritan Bennett LLC.

In various embodiments, based at least in part upon the value of the received signals corresponding to the light received by detector 30, the microprocessor 102 may calculate a physiological parameter using various algorithms. These algorithms may utilize coefficients, which may be empirically determined, corresponding to, for example, the wavelengths of light used. These may be stored in a ROM 144. In a two-wavelength system, the particular set of coefficients chosen for any pair of wavelength spectra may be determined by the value indicated by the encoder 140 corresponding to a particular light source in a particular sensor 14. For example, the first wavelength may be a wavelength that is highly sensitive to small quantities of deoxyhemoglobin in blood, and the second wavelength may be a complimentary wavelength. Specifically, for example, such wavelengths may be produced by orange, red, infrared, green, and/or yellow LEDs. Different wavelengths may be selected with control inputs 150. The control inputs 150 may be, for instance, a switch on the monitor, a keyboard, or a port providing instructions from a remote host computer.

In various embodiments, the monitor 12 may be connected to a network via a network interface 152. The network interface 152 may implement any networking technology or protocol, such as Ethernet, wireless Ethernet, and so forth. The network interface 152 may be connected to a network port 154 via a network cable or via a wireless connection. Additionally, the monitor 12 may include a non-volatile memory 160 that may store caregiver preferences, patient information, or any other information useful for configuring the monitor 12. The software for performing the configuration of the monitor 12 and retrieval of information over the network interface 152 may also be stored on the memory 160, or may be stored on the ROM 144.

The components of the monitor 12 may be configured to detect store, and utilize $SpO_2$ values at high resolution. In other words, the monitor 12 may estimate $SpO_2$ values at precisions of 0.1%, 0.01%, 0.001%, and so forth. Additionally, the monitor 12 may perform calculations and control algorithms based on these high resolution values. Further, the monitor 12 may be configured to correlate subtle changes in the $SpO_2$ values to large change in related parameters, such as $pO_2$, based on an inherent relationship between the parameters.

Pulse oximetry values of $SpO_2$ are generally only accurate to +/−1 or 2% precision with respect to invasively measured values of $SaO_2$. Accordingly, traditional pulse oximeters generally display values that are rounded to the nearest 1%. Further, inherent accuracy limitations in pulse oximetry may result in displaying an $SpO_2$ value that has been clipped at 100%. In other words, the displayed values of $SpO_2$ may be limited to 100% to address concerns that displaying a value greater than 100% may be misleading or confusing. For example, such clipping may occur in situations where supplemental oxygen is being utilized to treat a patient, and, due to inaccuracies, a calculated value of $SpO_2$ exceeds 100%. Specifically, for example, the $SpO_2$ value may be determined to be 102% and this value may be clipped to indicate a maximum value of 100% because an actual value of $SaO_2$ exceeding 100% would not be valid.

However, it is now recognized that the usual 1% $SpO_2$ reporting precision and the practice of clipping may limit the ability to detect subtle reentrant respiratory phenomena via $SpO_2$. Indeed, while pulse oximetry values of $SpO_2$ may be limited to +/−1 or 2% precision with respect to invasively measured values of $SaO_2$, it has now been recognized that the trending accuracy of $SpO_2$ is substantially more accurate. Indeed, once a pulse oximeter sensor is in place and not moved between observations, the changes in $SpO_2$ values have been determined to be quite accurate. In other words, the changes or differences between $SpO_2$ values correspond closely to the value of the actual changes or differences in the related $SaO_2$ values. Accordingly, present embodiments are directed to measuring and trending $SpO_2$ values that are measured with a precision in the tenths, hundredths, thousandths, and so forth. This facilitates detecting accurate and precise changes in $SpO_2$ and utilization of such detected changes in monitoring, control, and analysis.

Additionally, present embodiments may eliminate the artificial ceiling of 100% for calculated and/or displayed $SpO_2$ values. By eliminating such clipping, the changes that occur above an $SpO_2$ value of 100% may be utilized in accordance with present embodiments. For example, in one embodiment, a change in an $SpO_2$ value from 101.24% to 100.75% may be significant for control and/or monitoring. Specifically, for example, such a change may be significant with regard to monitoring and/or controlling $pO_2$, while remaining fairly insignificant with regard to monitoring $SpO_2$. Thus, by eliminating the ceiling of 100% and using changing high resolution $SpO_2$ values, present embodiments may include monitoring and control features that would be unavailable based on the use of less precise and/or clipped $SpO_2$ values.

Some embodiments in accordance with the present disclosure relate to systems and methods that use high-precision, unclipped $SpO_2$ values for the detection and/or characterization of subtle $SpO_2$ variations and/or patterns that may be indicative of clinically significant pathologies. For example, present embodiments may utilize trending or relative comparisons of small and precise $SpO_2$ values over time for detection and/or characterization of conditions relating to obstructive and/or central sleep apnea, hypopnea, hyperpnea, and/or Cheyne-Stokes syndrome.

A specific example in accordance with present embodiments may include a system that is configured to detect and/or assess issues relating to sleep apnea. Sleep apnea is generally described as a sleep disorder that is characterized by episodes of paused breathing during sleep. These episodes of paused breathing may occur repeatedly throughout sleep, and each episode may last long enough to cause one or more breaths to be missed. Such episodes may be referred to as apneas. A typical apnea may include an interval between breaths of at least 10 seconds, with a neurological arousal and/or a blood oxygen desaturation of 3% or greater. The actual duration and severity of each apnea may substantially vary between multiple patients. Further, duration and severity of apneas may vary throughout a period of sleep for a single patient. Indeed, sleep apnea may have a wide range of severity. Accordingly, it may be desirable to monitor precise $SpO_2$ levels, in accordance with present embodiments, to identify and/or assess potential indications of sleep apnea that could be overlooked by the less precise monitoring of traditional pulse oximetry systems. For example, small changes in $SpO_2$ levels over time may be utilized to ascertain subtle indications of sleep apnea.

Detection of subtle, yet pathological, $SpO_2$ variations may also be utilized in therapeutic systems and methods in accordance with present embodiments. In other words, changes occurring at high levels of precision, such as a change in the tenths or hundredths digit of a value of $SpO_2$, may be utilized to initiate therapy, control certain treatments (e.g., a rate of supplying supplemental oxygen), alert a caregiver to certain patient conditions, and so forth. For example, subtle changes in $SpO_2$ detected with high precision measurement may be utilized to reduce and/or block patient-controlled analgesia (PCA), recommend or titrate continuous positive air pressure (CPAP) therapy, or enable fine automatic adjustment of mechanical ventilation parameters (e.g., $FiO_2$, tidal volume, or respiratory rate). Indeed, such subtle changes may be utilized in a variety of different control algorithms to manage physiologic parameters and so forth.

One embodiment may include a system that is configured to control one or more physiologic parameters based on changes in the high precision component of the $SpO_2$ values or the like. Indeed, control of a patient's blood oxygen content with oxygen delivery is specifically discussed below as a particular example of present embodiments. However, one of ordinary skill in the art will recognize that this is merely one example and that different control parameters, delivery parameters, and the like may be utilized in accordance with present embodiments. For example, oxygen delivery may be adjusted based on a patient's estimated blood oxygen saturation level ($SpO_2$), oxygen delivery may be adjusted based on estimated $pO_2$ changes indicated by surrogate $SpO_2$ value changes, continuous positive airway pressure (CPAP) may be adjusted based on $SpO_2$, and/or patient-controlled analgesia may be inhibited during periods of low $SpO_2$. The small changes that are observable because of the added level of precision may facilitate such control mechanisms.

Figure 3:
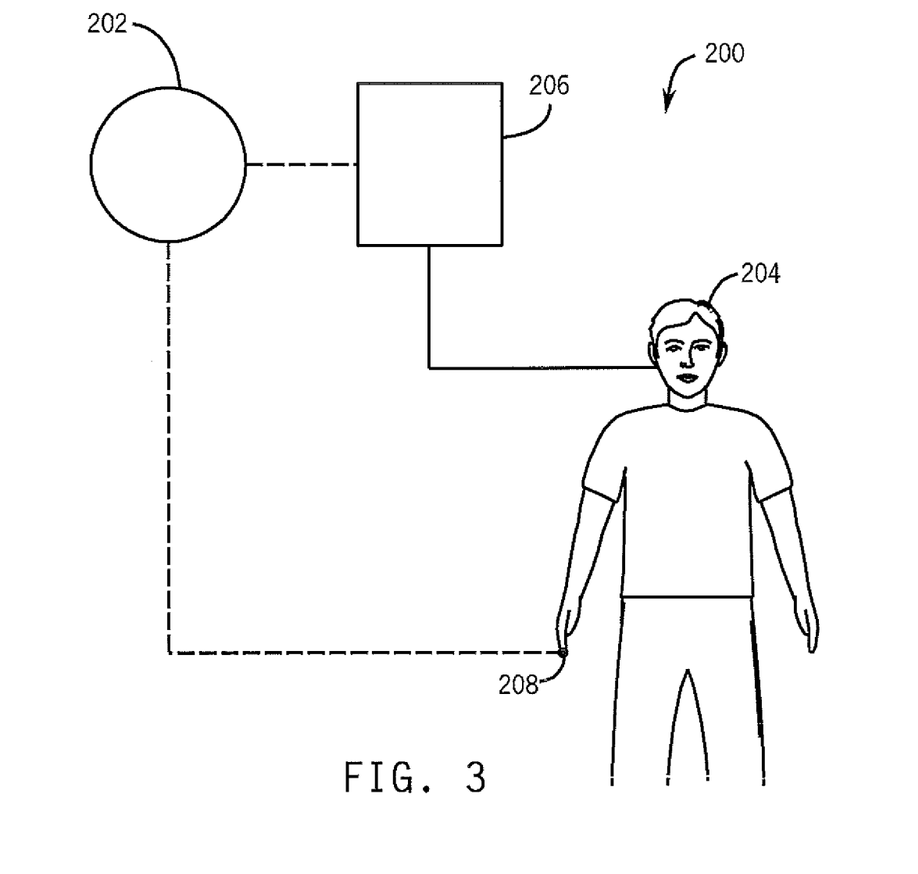
FIG. 3 is a block diagram of a physiologic parameter control system in accordance with an embodiment.

As indicated above, control of $SpO_2$ with oxygen delivery is presented herein as an example of a control feature in accordance with present embodiments. Specifically, FIG. 3 represents a system 200 including a controller 202 (e.g., a computer-based controller) that controls a composition and/or delivery amount of a gas mixture to a patient 204 to safely induce, maintain, and/or control the patient's $SpO_2$ level. Thus, in an example embodiment, a gas mixture supplied to the patient 204 may be considered the delivery parameter. For example, automatic adjustment of $FiO_2$ by the controller 202 may be utilized to control patient hypoxia or normoxia. $FiO_2$ may be defined as fractional inspired oxygen concentration or the percentage of oxygen in air inhaled by a patient through a ventilator. For example, in typical room air, the value for $FiO_2$ is approximately 21%.

In one embodiment a certain level of $SpO_2$ or $pO_2$ may be maintained within a narrow range by controlling based on the subtle changes in the high precision portion of the $SpO_2$ value (e.g., changes in a tenths, hundredths, or thousandths digit of an $SpO_2$ value). With regard to controlling $pO_2$, it should be noted that $SpO_2$ is a surrogate for $pO_2$ in blood. Precise ranges of control may be achieved in accordance with present embodiments by increasing and or decreasing $FiO_2$ based on the subtle changes in the $SpO_2$ value.

Indeed, as indicated above, changes illustrated by trending values have been found to be accurate. In other words, a change in the value of $SpO_2$ over time is an accurate reflection of the change in $SaO_2$ over the same time period) while the individual $SpO_2$ values themselves are not necessarily accurate representations of the $SaO_2$ value at each time. Thus, a change in the tenths, hundredths, or thousandths place of an $SpO_2$ value, or a changes at a higher level of precision may be utilized to make adjustments and control a physiologic parameter. This can be especially useful for parameters that have large changes relative to smaller changes in $SpO_2$ levels, such as $PO_2$. Such levels of control may assist in the prevention of certain issues that can arise due to inappropriate oxygen levels, such as retinopathy in neonates. Indeed, with regard to certain patients (e.g., neonates), a controller in accordance with present embodiments may maintain a very narrow range of $SpO_2$ levels, and, thus, $pO_2$ levels, to facilitate the avoidance of low oxygen level conditions associated with a risk for retinopathy, while avoiding high oxygen level conditions associated with lung development issues and the like.

The controller 202 may include a closed-loop $FiO_2$ controller that cooperates with a ventilator 206 to control the patient's $SpO_2$ value. Indeed, the controller 102 may receive input from a sensor 208 (e.g., a pulse oximeter sensor) that measures the patient's $SpO_2$ value at a high level of precision, and, based on a comparison of the measured $SpO_2$ value with a target $SpO_2$ value, manipulates the ventilator's output (e.g., $FiO_2$). For example, the $FiO_2$ controller 202 may output a request for increased $FiO_2$ from the ventilator 206 when a measured $SpO_2$ value is below a predefined $SpO_2$ target, or output a request for decreased $FiO_2$ from the ventilator 206 when the measured $SpO_2$ value is above the $SpO_2$ target By increasing or decreasing $FiO_2$, the patient's lungs may receive more or less oxygen, respectively, and the value of $SpO_2$ obtained from the patient will typically change correspondingly.

Figure 4:
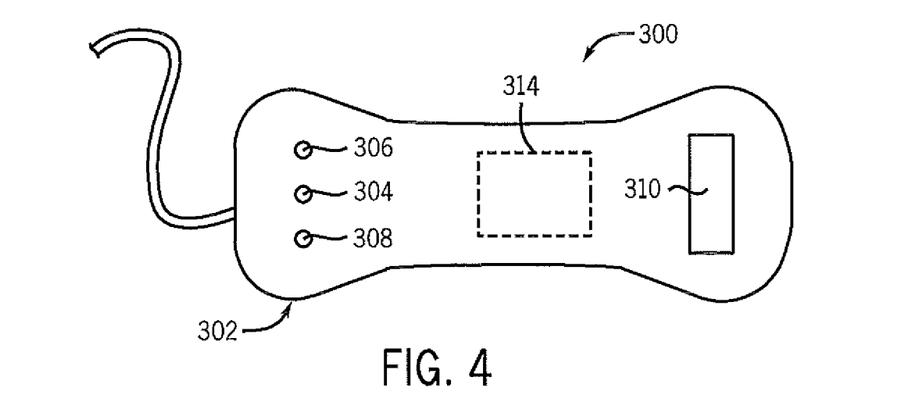
FIG. 4 is a perspective view of a sensor in accordance with an embodiment.

In accordance with present embodiments, detection of subtle variations in $SpO_2$ may be enhanced relative to the performance of traditional detectors by using an oximetry sensor that comprises light emitters with wavelengths selected for enhanced sensitivity to small changes in $SpO_2$. For example, FIG. 4 illustrates a sensor 300 in accordance with present embodiments, wherein the sensor 300 includes a plurality of light emitters 302. The plurality of light emitters 302 may include two or more emitters, wherein at least one of the light emitters 302 has a wavelength that facilitates detection of subtle variations in $SpO_2$. Indeed, the sensor 300 may include an emitter that is optimized for detection of small changes in $SpO_2$. Specifically, for example, the light emitters 302 may include a sensitivity optimized LED 304 that is capable of emitting light having a wavelength in the range of 600-680 nm. For example, in one embodiment, the LED 304 may emit light having a wavelength in the range of 600-620 nm. In another embodiment, the LED 304 may emit light having a wavelength near 660 nm. In the illustrated embodiment, the plurality of light emitters 302 includes the LED 304 and two other LEDs 306 and 308. In some embodiments, only the LED 304 and a second LED may be utilized. For example, the LED 304, which may be configured to emit light having a wavelength near 660 nm, may coordinate with the LED 306, which may be configured to emit light having a wavelength near 950 nm, to detect subtle $SpO_2$ variations. In one embodiment, the two LEDs 306 and 308 illustrated in FIG. 4 may have wavelengths that are more traditional for pulse oximetry. In another embodiment the two LEDs 306 and 308 may be optimized to provide light at wavelengths that specifically compliment the sensitivity function of the LED 304.

By including the LED 304, the LED 306, and/or the LED 308, the sensor 300 may be highly sensitive to small quantities of deoxyhemoglobin in blood, and, therefore, highly sensitive to small changes in $SpO_2$ at values nears 100% $SaO_2$. In other words, the light detected by a detector 310 of the sensor 300 may be largely impacted by small fluctuations in deoxyhemogloin because of the nature of the light emitted by the LED 304, the LED 306, and/or the LED 308. In the illustrated embodiment, the sensor 300 also includes a processor 314 that is capable of utilizing values related to detected light to calculate high resolution $SpO_2$ values and/or other blood characteristics.

Figure 5A:
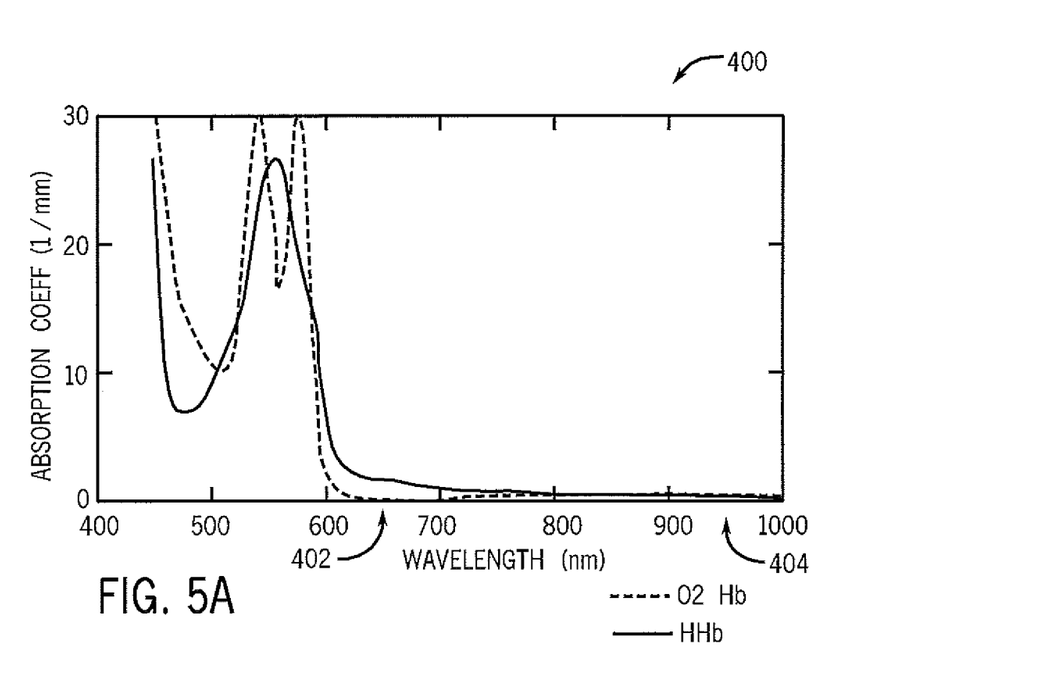
FIG. 5A, FIG. 5B, and FIG. 5C is a set of charts illustrating various variables plotted against wavelength to demonstrate optimization of sensor sensitivity in accordance with an embodiment.
Figure 5B:
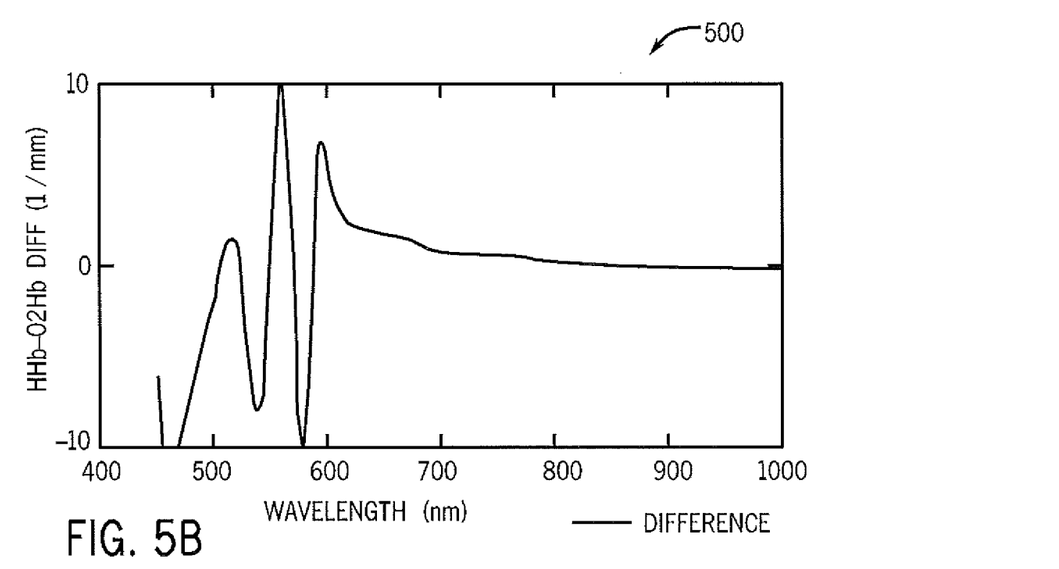
Figure 5C:
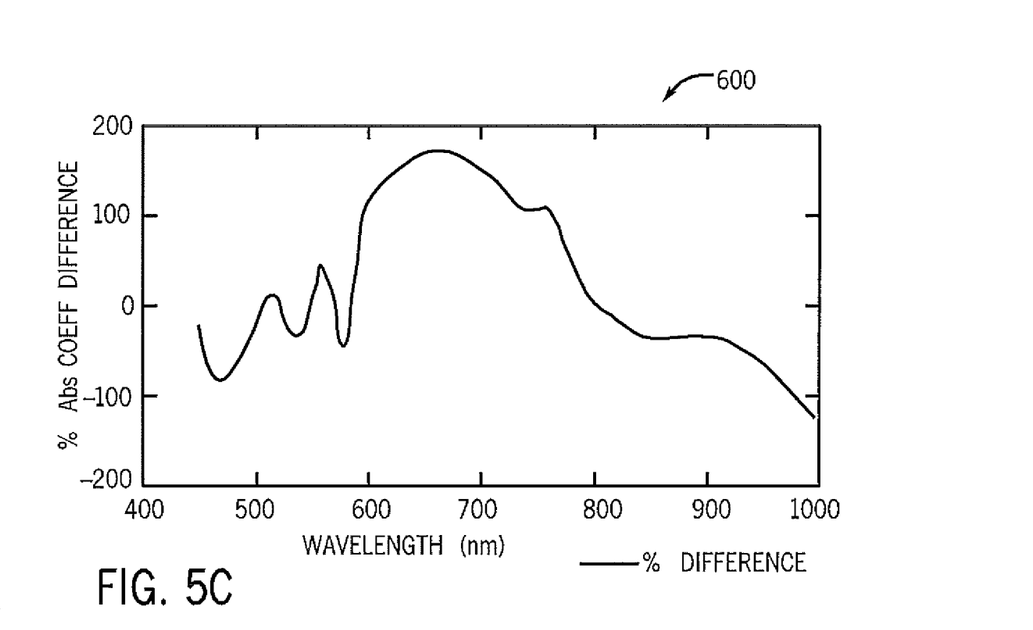

FIG. 5A includes a chart 400, which depicts absorption of oxyhemoglobin and deoxyhemoglobin plotted against wavelength. FIG. 5B includes a chart 500, which depicts an absorption coefficient difference plotted against wavelength. FIG. 5C includes a chart 600, which depicts a percent absolute coefficient difference plotted against wavelength. In the chart 400, in accordance with one embodiment, a selected range for the LED 304 is indicated by arrow 402 and a selected range for a second LED, such as LED 306, is indicated by arrow 404. The greatest slope in the modulation ratio versus saturation (normalized to the modulation ratio at 95% $SaO_2$) may be achieved by pairing the largest and smallest values in the chart 600 (e.g., wavelengths of 660 and 1000 nm or greater). However, since the photo-response of silicon detectors decreases significantly beyond approximately 950 nm, a wavelength near 950 nm may be a practical value to use. Thus, the sensor 300 may be utilized with other features in accordance with present embodiments to facilitate detection, analysis, and control based on high resolution changes in $SpO_2$ values.

Figure 6:
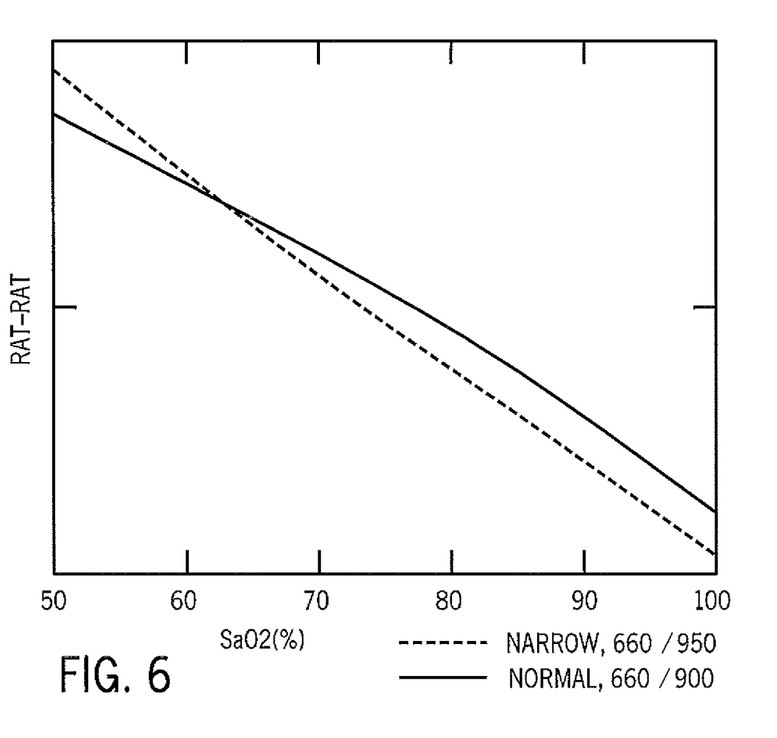
FIG. 6 is a chart illustrating modulation ratio plotted against blood oxygen saturation at different emitter-detector spacing to demonstrate sensor optimization in accordance with an embodiment.

It should be noted that in other embodiments, the LED 304 may include and/or be coordinated with a green or yellow LED. For example, a green LED may have a wavelength of 500-570 nm and a yellow LED may have a wavelength of 570-600 nm. These wavelengths may be beneficial because their greater absorption of hemoglobin may enable the detection of a stronger pulsatile signal that facilitates resolution of smaller changes in $SpO_2$. The encoder 140 should provide calibration information appropriate to whichever two or more wavelengths are used for calculation of $SpO_2$ or changes therein. Further, it should be noted adjusting the emitter-detector spacing may increase detection resolution. Indeed, moving the optics closer together in a reflectance design (though not so close as to create an optical shunt) may increase the slope of the modulation ratio relative to $SaO_2$, as shown in FIG. 6, wherein a 2-mm spacing (instead of 10 mm) at 660/950 results in −6.6% change in the modulation ratio per % $SaO_2$ (versus −5.6% per % $SaO_2$)

While the embodiments set forth in the present disclosure may be susceptible to various modifications and alternative forms, specific embodiments have been shown by way of example in the drawings and have been described in detail herein. However, it should be understood that the disclosure is not intended to be limited to the particular forms disclosed. Indeed, the present techniques may not only be applied to measurements of blood oxygen saturation, but these techniques may also be utilized for the measurement and/or analysis of other blood constituents. For example, using the same, different, or additional wavelengths, the present techniques may be utilized in conjunction with the measurement and/or analysis of carboxyhemoglobin, met-hemoglobin, total hemoglobin, intravascular dyes, and/or water content. The disclosure is to cover all modifications, equivalents, and alternatives falling within the spirit and scope of the disclosure as defined by the following appended claims.

What is claimed is:

1. A pulse oximetry system, comprising:
a sensor comprising: an emitter configured to emit light at different wavelengths into a tissue bed; and a detector configured to detect the light from the emitter after dispersion and/or reflection by the tissue bed; and
a pulse oximeter configured to:
receive signals from the sensor that are indicative of characteristics of the light detected by the detector;
utilize the signals to estimate blood oxygen saturation values over time at a high resolution;
detect variations in the blood oxygen saturation values that are smaller in magnitude than an accuracy, display precision, and/or calibration of the blood oxygen saturation values; and
perform control and/or pattern detection functions based on the variations.

2. The pulse oximetry system of claim 1, wherein the pulse oximeter is configured to estimate the blood oxygen saturation values with a precision of 0.1%, 0.01% or 0.001%.

3. The pulse oximetry system of claim 1, wherein the pulse oximeter is configured to report changes in a value of partial pressure of oxygen in blood based on the detection of variations in the blood oxygen saturation values.

4. The pulse oximetry system of claim 1, wherein the emitter is configured to emit light having a wavelength in a bounded range of 600-660 nm.

5. The pulse oximetry system of claim 4, wherein the emitter comprises at least two light emitting diodes, wherein one of the at least two light emitting diodes is configured to emit light in the bounded range of 600-620 nm.

6. A method of performing pulse oximetry, comprising:
emitting light from an emitter component of a pulse oximeter sensor at first and second wavelengths useful for measuring oxygen saturation;
detecting the light with a detector component of the pulse oximeter sensor;
transmitting signals indicative of characteristics of the detected light to a pulse oximeter;
estimating blood oxygen saturation values over time at a high resolution based on the signals with the pulse oximeter;
detecting variations in the blood oxygen saturation values that are smaller in magnitude than an accuracy, display precision, and/or calibration of the blood oxygen saturation values; and
detecting a patient condition and/or controlling a physiologic parameter based on the variations.

7. The method of claim 6, wherein the first wavelength is between 650-670 nm.

8. The method of claim 6, wherein the first wavelength is within a range of 600-620 nm and the second wavelength is within a range of 800-940 nm.

9. The method of claim 6, comprising controlling a partial pressure of oxygen in a patient's blood based on the variations in the blood oxygen saturation values.

10. The method of claim 9, wherein controlling the partial pressure of oxygen comprises controlling delivery of oxygen to the patient based on the variations in the blood oxygen saturation values.

11. The method of claim 6, comprising identifying a pattern indicative of sleep apnea based on the variations in the blood oxygen saturation values.

12. The method of claim 6, comprising displaying the blood oxygen saturation values at the high resolution on a display screen.

13. A pulse oximeter sensor configured to facilitate detection of high precision changes in blood oxygen saturation estimates obtained via pulse oximetry, comprising:
a sensor body;
a plurality of emitters positioned within the sensor body, wherein each of the plurality of emitters is configured to emit light at a different wavelength, and wherein at least one of the plurality of emitters is selected for sensitivity to small changes in blood oxygen saturation by emitting light within a bounded range of wavelengths;
a detector configured to detect the light emitted by the plurality of emitters; and
a processor configured to calculate a value of blood oxygen saturation based on the detected light with a precision of 0.1, 0.01, or 0.001.

14. The pulse oximeter sensor of claim 13, wherein one of the plurality of emitters is configured to emit light having a wavelength in a bounded range of 600-620 nm.

15. The pulse oximeter sensor of claim 13, wherein one of the plurality of emitters is configured to emit light having a wavelength between 650-670 nm and another one of the plurality of emitters is configured to emit light having a wavelength between 940-1000 nm.

16. The pulse oximeter sensor of claim 14, wherein the plurality of emitters comprise an orange LED configured to emit light having a wavelength in a bounded range of 600-620 nm, and an infrared LED configured to emit light having a wavelength in a bounded range of 800-940 nm.

17. The pulse oximeter sensor of claim 14, wherein the plurality of emitters comprise an orange LED configured to emit light having a wavelength in a bounded range of 600-620 nm, and a red LED configured to emit light having a wavelength in a bounded range of 640-740 nm.

* * * * *